(12) United States Patent
Arimori et al.

(10) Patent No.: US 8,304,437 B2
(45) Date of Patent: Nov. 6, 2012

(54) CARBOXAMIDE COMPOUND AND USE OF THE SAME

(75) Inventors: Sadayuki Arimori, Toyonaka (JP); Yoshiharu Kinoshita, Misawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/071,630

(22) Filed: Mar. 25, 2011

(65) Prior Publication Data
US 2011/0172276 A1    Jul. 14, 2011

Related U.S. Application Data

(62) Division of application No. 11/919,077, filed as application No. PCT/JP2006/308500 on Apr. 18, 2006, now Pat. No. 7,935,716.

(30) Foreign Application Priority Data

May 31, 2005 (JP) ................................. 2005-158568
Nov. 28, 2005 (JP) ................................. 2005-341610

(51) Int. Cl.
*A61K 31/4436* (2006.01)
*C07D 417/12* (2006.01)
(52) U.S. Cl. .................... 514/342; 546/270.7
(58) Field of Classification Search ............... 546/270.7; 514/342
See application file for complete search history.

(56) References Cited

FOREIGN PATENT DOCUMENTS

| JP | 5-286970 A | 11/1993 |
|---|---|---|
| JP | 8-67671 A | 3/1996 |
| JP | 10-195072 A | 7/1998 |
| JP | 2003-528806 A | 9/2003 |
| JP | 2005-53843 A | 3/2005 |
| WO | WO 01/05769 A2 | 1/2001 |

OTHER PUBLICATIONS

Gertzmann et al., "A catalyst system for formation of amides by reaction of carboxylic acids with blocked isocyanates," Tetrahedron Letters, vol. 46, pp. 6659-6662 (2005).

*Primary Examiner* — Patricia Morris
(74) *Attorney, Agent, or Firm* — Birch, Stewart, Kolasch & Birch, LLP

(57) ABSTRACT

A carboxamide compound represented by the formula (I):

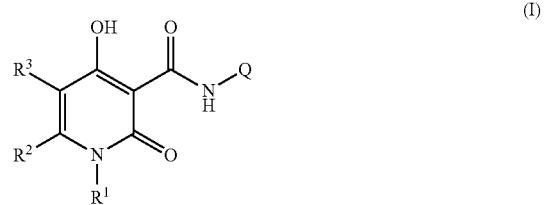

[wherein Q represents a nitrogen-containing 5-membered heterocyclic group optionally fused with a benzene ring, $R^1$ represents a C1-C3 alkyl group or the like, $R^2$ represents a hydrogen atom or the like, and $R^3$ represents a hydrogen atom.] has an excellent plant disease controlling effect.

4 Claims, No Drawings

CARBOXAMIDE COMPOUND AND USE OF THE SAME

This application is a Divisional of application Ser. No. 11/919,077 filed Oct. 23, 2007 (which issued as U.S. Pat. No. 7,935,716 B1 on May 3, 2011) for which priority is claimed under 35 U.S.C. §120, which is the national phase of PCT International. Application No. PCT/JP2006/308500 filed on Apr. 18, 2006 under 35 U.S.C. §371. The entire contents of each of the above-identified applications are hereby incorporated by reference.

TECHNICAL FIELD

The present invention relates to a carboxamide compound, and use of the same.

BACKGROUND ART

Development of a plant disease controlling agent has been progressed, and many compounds having controlling activity against plant diseases have been found out. However, plant disease controlling activity of these compounds is not sufficient in some cases.

Novel compounds having plant disease controlling activity have been investigated intensively.

DISCLOSURE OF THE INVENTION

An object of the present invention is to provide a compound having excellent plant disease controlling activity.

The present invention is as follows:

[1] A carboxamide compound represented by the formula (I):

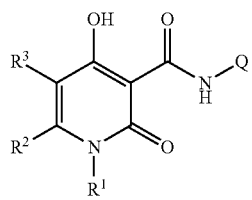

[wherein Q represents a nitrogen-containing 5-membered heterocyclic group optionally fused with a benzene ring, and the heterocyclic group may be substituted with at least one group selected from the group consisting of a halogen atom, a cyano group, a C1-C3 alkyl group and a C1-C3 haloalkyl group, $R^1$ represents a C1-C3 alkyl group or a C2-C5 alkoxyalkyl group, $R^2$ represents a hydrogen atom or a C1-C3 alkyl group, or $R^1$ and $R^2$ bind to each other at an end to represent a C3-C4 alkylene group and $R^3$ represents a hydrogen atom, a halogen atom or a C1-C3 alkyl group.] (hereinafter, referred to as present compound).

[2] The carboxamide compound according to [1], wherein Q is a nitrogen-containing 5-membered heterocyclic group optionally fused with a benzene ring, and the heterocyclic group may be substituted with at least one group selected from the group consisting of a halogen atom, a cyano group, a C1-C3 alkyl group and a C1-C3 haloalkyl group, and a carbon atom adjacent to a nitrogen atom among ring constitutional atoms and a nitrogen atom of NH in the formula (I) bind to each other.

[3] The carboxamide compound according to [1], wherein Q is a nitrogen-containing 5-membered heterocyclic group optionally fused with a benzene ring, the heterocyclic group may be substituted with at least one group selected from the group consisting of a halogen atom, a cyano group, a C1-C3 alkyl group and a C1-C3 haloalkyl group, and the heterocyclic group has as a ring constitutional atom one nitrogen atom, and at least one hetero atom selected from an oxygen atom, a sulfur atom and a nitrogen atom.

[4] The carboxamide compound according to [1], wherein Q is a nitrogen-containing 5-membered heterocyclic group not fused with other ring, and the heterocyclic group may be substituted with at least one group selected from the group consisting of a halogen atom, a cyano group, a C1-C3 alkyl group and a C1-C3 haloalkyl group.

[5] The carboxamide compound according to [1], wherein Q is a nitrogen-containing 5-membered heterocyclic group fused with a benzene ring, and the heterocyclic group may be substituted with at least one group selected from the group consisting of a halogen atom, a cyano group, a C1-C3 alkyl group and a C1-C3 haloalkyl group.

[6] The carboxamide compound according to [1], wherein Q is a heterocyclic group which is a thiazolyl group, a benzothiazolyl group, an imidazolyl group, a benzimidazolyl group, a pyrazolyl group, a 1,2,4-oxadiazolyl group, a 1,2,4-thiadiazolyl group, a 1,2,4-triazolyl group, a 1,3,4-oxadiazolyl group or a 1,3,4-thiadiazolyl group, and the heterocyclic group may be substituted with at least one group selected from the group consisting of a halogen atom, a cyano group, a C1-C3 alkyl group and a C1-C3 haloalkyl group.

[7] The carboxamide compound according to [1], wherein Q is a heterocyclic group which is a 2-thiazolyl group, a 2-benzothiazolyl group, a 2-imidazolyl group, a 2-benzimidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and C1-C3 haloalkyl group.

[8] The carboxamide compound according to [1], wherein Q is a heterocyclic group which is a 2-thiazolyl group, a 2-imidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and a C1-C3 haloalkyl group.

[9] The carboxamide compound according to [1], wherein Q is a heterocyclic group which is a 2-benzothiazolyl group or a 2-benzimidazolyl group, and the heterocyclic group may be substituted with at least one group selected from the group consisting of a halogen atom, a cyano group, a C1-C3 alkyl group and a C1-C3 haloalkyl group.

[10] The carboxamide compound according to [1], wherein Q is a 2-benzimidazolyl group optionally substituted with at least one group selected from the group consisting of a halogen atom, a cyano group, a C1-C3 alkyl group and a C1-C3 haloalkyl group.

[11] The carboxamide compound according to any one of [1] to [10], wherein $R^3$ is a hydrogen atom or a C1-C3 alkyl group.

[12] The carboxamide compound according to any one of [1] to [10], wherein $R^3$ is a hydrogen atom or a halogen atom.

[13] A plant disease controlling agent comprising the carboxamide compound as defined in any one of [1] to [12] as an active ingredient, and an inert carrier.

[14] A method of controlling a plant disease, comprising a step of treating a plant or a soil where a plant grows with an effective amount of the carboxamide compound as defined in any one of [1] to [12].

[15] Use of the carboxamide compound as defined in any one of [1] to [12] for controlling a plant disease.

In the present invention, as groups represented by Q, $R^1$, $R^2$ and $R^3$, the following specific examples are mentioned.

The C1-C3 alkyl group represented by $R^1$ include a methyl group, an ethyl group, a propyl group and an isopropyl group, and examples of the C2-C5 alkoxyalkyl group include a methoxymethyl group, an ethoxymethyl group and a propoxymethyl group.

The C1-C3 alkyl group represented by $R^2$ include a methyl group, an ethyl group, a propyl group and an isopropyl group.

Examples of the C3-C4 alkylene group in which $R^1$ and $R^2$ are bound to each other at an end include a trimethylene group and a tetramethylene group.

The halogen atom represented by $R^3$ include a fluorine atom, a chlorine atom, a bromine atom and an iodine atom.

The C1-C3 alkyl group represented by $R^3$ include a methyl group, an ethyl group, a propyl group and an isopropyl group.

Q represents a nitrogen-containing 5-membered heterocyclic group optionally fused with a benzene ring. The nitrogen-containing 5-membered heterocyclic group optionally fused with a benzene ring may be substituted with at least one group selected from the group consisting of a halogen atom (e.g., a fluorine atom or a chlorine atom), a cyano group, a C1-C3 alkyl group (e.g., a methyl group, an ethyl group or a propyl group) and a C1-C3 haloalkyl group (e.g., a trifluoromethyl group), at the 5-membered ring part and/or benzene ring part. Examples of the heterocyclic group represented by Q include the following groups.

A nitrogen-containing 5-membered heterocyclic group optionally fused with a benzene ring in which the heterocyclic group may be substituted with at least one group selected from the group consisting of a halogen atom, a cyano group, a C1-C3 alkyl group and a C1-C3 haloalkyl group and a carbon atom adjacent to a nitrogen atom among ring constitutional atoms and a nitrogen atom of NH in the formula (I) bind to each other.

A nitrogen-containing 5-membered heterocyclic group optionally fused with a benzene ring in which the heterocyclic group may be substituted with at least one group selected from the group consisting of a halogen atom, a cyano group, a C1-C3 alkyl group and a C1-C3 haloalkyl group and the heterocyclic group has one nitrogen atom, and at least one hetero atom selected from an oxygen atom, sulfur atom and nitrogen atom as a ring constitutional atom.

A nitrogen-containing 5-membered heterocyclic group not fused with other ring in which the heterocyclic group may be substituted with at least one group selected from the group consisting of a halogen atom, a cyano group, a C1-C3 alkyl group and a C1-C3 haloalkyl group.

A nitrogen-containing 5-membered heterocyclic group fused with a benzene ring in which the heterocyclic group may be substituted with at least one group selected from the group consisting of a halogen atom, a cyano group, a C1-C3 alkyl group and a C1-C3 haloalkyl group, on the 5-membered ring and/or benzene ring.

A heterocyclic group represented by the formula (a-1) or the formula (a-2):

[wherein, $Z^1$ represents an oxygen atom, a sulfur atom or $NA^1$, $Z^2$ represents a nitrogen atom or $CA^2$ group, and $Z^3$ represents a nitrogen atom or $CA^3$ group, $A^1$ represents a hydrogen atom or C1-C3 alkyl group (e.g., a methyl group, an ethyl group or a propyl group), $A^2$ represents a hydrogen atom, halogen atom (e.g., a fluorine atom or a chlorine atom), a cyano group, a C1-C3 alkyl group (e.g., a methyl group, an ethyl group or a propyl group) or a C1-C3 haloalkyl group (e.g., a trifluoromethyl group), $A^3$ represents a hydrogen atom, a halogen atom (e.g., a fluorine atom or a chlorine atom), a cyano group, a C1-C3 alkyl group (e.g., a methyl group, an ethyl group or a propyl group) or a C1-C3 haloalkyl group (e.g., a trifluoromethyl group), or $A^2$ and $A^3$ bind to each other at an end to represent a 1,3-butadiene-1,4-diyl group optionally substituted with a halogen atom, a cyano group, a C1-C3 alkyl group or a C1-C3 haloalkyl group (e.g., 1,3-butadiene-1,4-diyl group, 2-fluoro-1,3-butadiene-1,4-diyl group, 2-chloro-1,3-butadiene-1,4-diyl group, 2-cyano-1,3-butadiene-1,4-diyl group, 2-methyl-1,3-butadiene-1,4-diyl group, 2-trifluoromethyl-1,3-butadiene-1,4-diyl group, 1-fluoro-1,3-butadiene-1,4-diyl group, 1-chloro-1,3-butadiene-1,4-diyl group and 1-methyl-1,3-butadiene-1,4-diyl group). Here, if $Z^1$ is $NA^1$ and $A^1$ is a hydrogen atom, then, $Z^2$ is a $CA^2$ group and $Z^3$ is a $CA^3$ group.

$Z^4$ represents an oxygen atom, a sulfur atom or $NA^4$, $Z^5$ represents a nitrogen atom or $CA^5$, and $Z^6$ represents a nitrogen atom or $CA^6$, $A^4$ represents a hydrogen atom or C1-C3 alkyl group (e.g., a methyl group, an ethyl group or a propyl group), $A^5$ represents a hydrogen atom or C1-C3 alkyl group (e.g., a methyl group, an ethyl group or a propyl group), and $A^6$ represents a hydrogen atom or a C1-C3 alkyl group (e.g., a methyl group, an ethyl group or a propyl group).].

A heterocyclic group which is a thiazolyl group, benzothiazolyl group, an imidazolyl group, a benzimidazolyl group, a pyrazolyl group, a 1,2,4-oxadiazolyl group, a 1,2,4-thiadiazolyl group, a 1,2,4-thiazolyl group, a 1,3,4-oxadiazolyl group or a 1,3,4-thiadiazolyl group in which the heterocyclic group may be substituted with at least one group selected from the group consisting of a halogen atom, a cyano group, a C1-C3 alkyl group and a C1-C3 haloalkyl group.

A heterocyclic group which is a 2-thiazolyl group, a 2-benzothiazolyl group, a 2-imidazolyl group, a 2-benzimidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group in which the heterocyclic group may be substituted with at least one group selected from the group consisting of a halogen atom, a cyano group, a C1-C3 alkyl group and a C1-C3 haloalkyl group.

Specific examples of the heterocyclic group represented by Q include a2-imidazolyl group, a4-methyl-2-imidazolyl group, a 4,5-dimethyl-2-imidazolyl group, a 4-chloro-2-imidazolyl group, a 4-bromo-2-imidazolyl group, a 4,5-dicyano-2-imidazolyl group, a 4-fluoro-2-imidazolyl group, a 4-cyano-2-imidazolyl group, a 2-benzimidazolyl group, a 4-fluoro-2-benzimidazolyl group, a 5-fluoro-2-benzimidazolyl group, a 4-chloro-2-benzimidazolyl group, a 5-chloro-2-benzimidazolyl group, a 4-cyano-2-benzimidazolyl group, a 5-cyano-2-benzimidazolyl group, a 4-methyl-2-benzimidazolyl group, a 5-methyl-2-benzimidazolyl group, a 4-trifluoromethyl-2-benzimidazolyl group, a 5-trifluoromethyl-2-benzimidazolyl group, a 5,6-dimethyl-2-benzimidazolyl group, a 5,6-difluoro-2-benzimidazolyl group, a 5,6-dichloro-2-benzimidazolyl group, a 5-trifluoromethyl-2-benzimidazolyl group, a 5-cyano-2-benzimidazolyl group, a 2-thiazolyl group, a 4-methyl-2-thiazolyl group, a 4,5-dimethyl-2-thiazolyl group, a 4-chloro-2-thiazolyl group, a 4-bromo-2-thiazolyl group, a 4,5-dicyano-2-thiazolyl group, a 4-fluoro-2-thiazolyl group, a 4-cyano-2-thiazolyl group, a 2-benzothiazolyl group, a 4-fluoro-2-benzothiazolyl group, a 5-fluoro-2-benzothiazolyl group, a 6-fluoro-2-benzothiazolyl group, a 7-fluoro-2-benzothiazolyl group, a 4-chloro-2-benzothiazolyl group, a 5-chloro-2-benzothiazolyl group, a 6-chloro-2-benzothiazolyl group, a 7-chloro-2-benzothiazolyl group, a 4-methyl-2-benzothiazolyl group, a 5-methyl-2-benzothiazolyl group, a 6-methyl-2-benzothiazolyl group, a 7-methyl-2-benzothiazolyl group, a 5,6-dimethyl-2-benzothiazolyl group, a 5,6-difluoro-2-benzothiazolyl group, a 5,6-dichloro-2-benzothiazolyl group, a 5-trifluoromethyl-2-benzothiazolyl group, a 5-cyano-2-benzothiazolyl group, a 1-methyl-3-pyrazolyl group, a 1,5-dimethyl-3-pyrazolyl group, a 4-chloro-1-methyl-3-pyrazolyl group, a 1-ethyl-3-pyrazolyl group, a 1-(2,2,2-trifluoroethyl)-3-pyrazolyl group, a 1,2,4-thiadiazol-5-yl group, a 3-methyl-1,2,4-thiadiazol-5-yl group, a 3-trifluoromethyl-1,2,4-thiadiazol-5-yl group, a 3-cyano-1,2,4-thiadiazol-5-yl group, a 1,3,4-thiadiazol-2-yl group, a 5-methyl-1,3,4-thiadiazol-2-yl group, a 5-trifluoromethyl-1,3,4-thiadiazol-2-yl group and a 5-cyano-1,3,4-thiadiazol-2-yl group.

Embodiments of the present compound include, for example, the following compounds among the present compounds.

A carboxamide compound represented by the formula (I) in which Q is a nitrogen-containing 5-membered heterocyclic group optionally fused with a benzene ring, the heterocyclic group may be substituted with at least one group selected from the group consisting of a halogen atom, a cyano group, a C1-C3 alkyl group and a C1-C3 haloalkyl group, and the heterocyclic group has one nitrogen atom, and at least one hetero atom selected from an oxygen atom, a sulfur atom and a nitrogen atom as a ring constitutional atom.

A carboxamide compound represented by the formula (I) in which Q is a nitrogen-containing 5-membered heterocyclic group optionally fused with a benzene ring, the heterocyclic group may be substituted with at least one group selected from the group consisting of a halogen atom, a cyano group, a C1-C3 alkyl group and a C1-C3 haloalkyl group, and a carbon atom adjacent to a nitrogen atom among ring constitutional atoms and a nitrogen atom of NH in the formula (I) bind to each other.

A carboxamide compound represented by the formula (I) in which Q is a nitrogen-containing 5-membered heterocyclic group not fused with other ring, and the heterocyclic group may be substituted with at least one group selected from the group consisting of a halogen atom, a cyano group, a C1-C3 alkyl group and a C1-C3 haloalkyl group;

A carboxamide compound represented by the formula (I) in which Q is a nitrogen-containing 5-membered heterocyclic group fused with a benzene ring, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which Q is a heterocyclic group represented by the formula (a-1) or the formula (a-2):

[wherein, $Z^1$ represents an oxygen atom, a sulfur atom or $NA^1$, $Z^2$ represents a nitrogen atom or $CA^2$ group, $Z^3$ represents a nitrogen atom or $CA^3$ group, $A^1$ represents a hydrogen atom or a C1-C3 alkyl group, $A^2$ represents a hydrogen atom, a halogen atom, cyano group, a C1-C3 alkyl group or a C1-C3 haloalkyl group, $A^3$ represents a hydrogen atom, a halogen atom, a cyano group, a C1-C3 alkyl group or a C1-C3 haloalkyl group, or $A^2$ and $A^3$ bind to each other at an end to represent a 1,3-butadiene-1,4-diyl group optionally substituted with a halogen atom, a cyano group, C1-C3 alkyl group or a C1-C3 haloalkyl group. Here, if $Z^1$ is $NA^1$ and $A^1$ is a hydrogen atom, then, $Z^2$ is a $CA^2$ group and $Z^3$ is a $CA^3$ group.

$Z^4$ represents an oxygen atom, a sulfur atom or $NA^4$, $Z^5$ represents a nitrogen atom or $CA^5$, and $Z^6$ represents a nitrogen atom or $CA^6$, $A^4$ represents a hydrogen atom or a C1-C3 alkyl group, $A^5$ represents a hydrogen atom or a C1-C3 alkyl group, and $A^6$ represents a hydrogen atom or a C1-C3 alkyl group.].

A carboxamide compound represented by the formula (I) in which Q is a heterocyclic group which is a thiazolyl group, a benzothiazolyl group, an imidazolyl group, a benzimidazolyl group, a pyrazolyl group, a 1,2,4-oxadiazolyl group, a 1,2,4-thiadiazolyl group, a 1,2,4-triazolyl group, a 1,3,4-oxadiazolyl group or a 1,3,4-thiadiazolyl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which Q is a heterocyclic group which is a 2-thiazolyl group, a 2-benzothiazolyl group, a 2-imidazolyl group, a 2-benzimidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which Q is a heterocyclic group which is a 2-thiazolyl group, a 2-imidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which Q is a heterocyclic group which is a 2-benzothiazolyl group or a 2-benzimidazolyl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which Q is a 2-benzimidazolyl group optionally substituted with at least one group selected from the group consisting of a halogen atom, a cyano group, a C1-C3 alkyl group and a C1-C3 haloalkyl group.

A carboxamide compound represented by the formula (I) in which Q is a 2-imidazolyl group, a 4-methyl-2-imidazolyl group, a 4,5-dimethyl-2-imidazolyl group, a 4-chloro-2-imidazolyl group, a 4-bromo-2-imidazolyl group, a 4,5-dicyano-2-imidazolyl group, a 4-fluoro-2-imidazolyl group or a 4-cyano-2-imidazolyl group.

A carboxamide compound represented by the formula (I) in which Q is a 2-benzimidazolyl group, a 4-fluoro-2-benzimidazolyl group, a 5-fluoro-2-benzimidazolyl group, a 4-chloro-2-benzimidazolyl group, a 5-chloro-2-benzimidazolyl group, a 4-methyl-2-benzimidazolyl group, a 5-methyl-2-benzimidazolyl group, a 5,6-dimethyl-2-benzimidazolyl group, a 5,6-difluoro-2-benzimidazolyl group, a 5,6-dichloro-2-benzimidazolyl group, a 5-trifluoromethyl-2-benzimidazolyl group or a 5-cyano-2-benzimidazolyl group.

A carboxamide compound represented by the formula (I) in which Q is a 2-thiazolyl group, a 4-methyl-2-thiazolyl group, a 4,5-dimethyl-2-thiazolyl group, a 4-chloro-2-thiazolyl group, a 4-bromo-2-thiazolyl group, a 4,5-dicyano-2-thiazolyl group, a 4-fluoro-2-thiazolyl group or a 4-cyano-2-thiazolyl group.

A carboxamide compound represented by the formula (I) in which Q is a 2-benzothiazolyl group, a 4-fluoro-2-benzothiazolyl group, a 5-fluoro-2-benzothiazolyl group, a 6-fluoro-2-benzothiazolyl group, a 7-fluoro-2-benzothiazolyl group, a 4-chloro-2-benzothiazolyl group, a 5-chloro-2-benzothiazolyl group, a 6-chloro-2-benzothiazolyl group, a 7-chloro-2-benzothiazolyl group, a 4-methyl-2-benzothiazolyl group, a 5-methyl-2-benzothiazolyl group, a 6-methyl-2-benzothiazolyl group, a 7-methyl-2-benzothiazolyl group, a 5,6-dimethyl-2-benzothiazolyl group, a 5,6-difluoro-2-benzothiazolyl group, a 5,6-dichloro-2-benzothiazolyl group, a 5-trifluoromethyl-2-benzothiazolyl group or a 5-cyano-2-benzothiazolyl group.

A carboxamide compound represented by the formula (I) in which Q is a 1,2,4-thiadiazol-5-yl group, a 3-methyl-1,2,4-thiadiazol-5-yl group, a 3-trifluoromethyl-1,2,4-thiadiazol-5-yl group or a 3-cyano-1,2,4-thiadiazol-5-yl group.

A carboxamide compound represented by the formula (I) in which Q is a 1,3,4-thiadiazol-2-yl group, a 5-methyl-1,3,4-thiadiazol-2-yl group, a 5-trifluoromethyl-1,3,4-thiadiazol-2-yl group or a 5-cyano-1,3,4-thiadiazol-2-yl group.

A carboxamide compound represented by the formula (I) in which $R^2$ is a hydrogen atom and $R^3$ is a hydrogen atom or a C1-C3 alkyl group.

A carboxamide compound represented by the formula (I) in which $R^2$ is a methyl group and $R^3$ is a hydrogen atom or a C1-C3 alkyl group.

A carboxamide compound represented by the formula (I) in which $R^2$ is a hydrogen atom and $R^3$ is a hydrogen atom or a C1-C3 alkyl group.

A carboxamide compound represented by the formula (I) in which $R^1$ is a methyl group, $R^2$ is a hydrogen atom, and $R^3$ is a hydrogen atom or a C1-C3 alkyl group.

A carboxamide compound represented by the formula (I) in which $R^1$ is a methyl group, $R^2$ is a methyl group, and $R^3$ is a hydrogen atom or a C1-C3 alkyl group.

A carboxamide compound represented by the formula (I) in which $R^1$ is a methyl group, $R^2$ is a hydrogen atom, and $R^3$ is a hydrogen atom or a C1-C3 alkyl group.

A carboxamide compound represented by the formula (I) in which $R^1$ and $R^2$ bind to each other at an end to form a trimethylene group, and $R^3$ is a hydrogen atom or a C1-C3 alkyl group.

A carboxamide compound represented by the formula (I) in which $R^3$ is a hydrogen atom or a C1-C3 alkyl group, Q is a nitrogen-containing 5-membered heterocyclic group optionally fused with a benzene ring, the heterocyclic group may be substituted with at least one group selected from the group consisting of a halogen atom, a cyano group, a C1-C3 alkyl group and a C1-C3 haloalkyl group and the heterocyclic group has one nitrogen atom, and at least one hetero atom selected from an oxygen atom, a sulfur atom and a nitrogen atom as a ring constitutional atom.

A carboxamide compound represented by the formula (I) in which $R^3$ is a hydrogen atom or a C1-C3 alkyl group, Q is a nitrogen-containing 5-membered heterocyclic group optionally fused with a benzene ring, the heterocyclic group may be substituted with at least one group selected from the group consisting of a halogen atom, a cyano group, a C1-C3 alkyl group and a C1-C3 haloalkyl group; and a carbon atom adjacent to a nitrogen atom among ring constitutional atoms and a nitrogen atom of NH in the formula (I) bind to each other.

A carboxamide compound represented by the formula (I) in which $R^3$ is a hydrogen atom or a C1-C3 alkyl group, Q is a nitrogen-containing 5-membered heterocyclic group not fused with other ring, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, Q is a nitrogen-containing 5-membered heterocyclic group fused with a benzene ring, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, and Q is a heterocyclic group represented by the formula (a-1) or the formula (a-2):

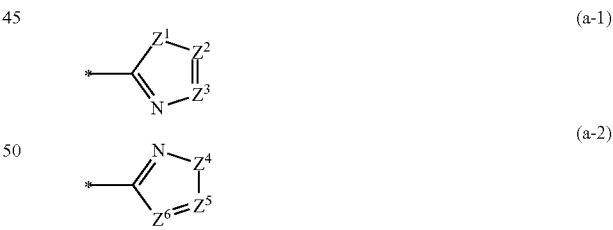

[wherein, $Z^1$ represents an oxygen atom, a sulfur atom or $NA^1$, $Z^2$ represents a nitrogen atom or $CA^2$ group, $Z^3$ represents a nitrogen atom or $CA^3$ group, $A^1$ represents a hydrogen atom or a C1-C3 alkyl group, $A^2$ represents a hydrogen atom, a halogen atom, cyano group, a C1-C3 alkyl group or a C1-C3 haloalkyl group, $A^3$ represents a hydrogen atom, a halogen atom, a cyano group, a C1-C3 alkyl group or a C1-C3 haloalkyl group, or $A^2$ and $A^3$ may bind to each other at an end to represent a 1,3-butadiene-1,4-diyl group optionally substituted with a halogen atom, a cyano group, a C1-C3 alkyl group or a C1-C3 haloalkyl group. Here, if $Z^1$ is $NA^1$ and $A^1$ is a hydrogen atom, then, $Z^2$ is a $CA^2$ group and $Z^3$ is a $CA^3$ group.

$Z^4$ represents an oxygen atom, sulfur atom or $NA^4$, $Z^5$ represents a nitrogen atom or $CA^5$, and $Z^6$ represents a nitrogen atom or $CA^6$, $A^4$ represents a hydrogen atom or a C1-C3 alkyl group, $A^5$ represents a hydrogen atom or a C1-C3 alkyl group, and $A^6$ represents a hydrogen atom or a C1-C3 alkyl group.].

A carboxamide compound represented by the formula (I) in which $R^3$ is a hydrogen atom or a C1-C3 alkyl group, Q is a heterocyclic group which is a thiazolyl group, a benzothiazolyl group, an imidazolyl group, a benzimidazolyl group, a pyrazolyl group, a 1,2,4-oxadiazolyl group, a 1,2,4-thiadiazolyl group, a 1,2,4-triazolyl group, a 1,3,4-oxadiazolyl group or a 1,3,4-thiadiazolyl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, Q is a heterocyclic group which is a 2-thiazolyl group, a 2-benzothiazolyl group, a 2-imidazolyl group, a 2-benzimidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, Q is a heterocyclic group which is a 2-thiazolyl group, a 2-imidazolyl group, a 3-pyrazolyl group, a 1,2,4-oxadiazol-5-yl group, a 1,2,4-thiadiazol-5-yl group, a 1,2,4-triazol-3-yl group, a 1,3,4-oxadiazol-2-yl group or a 1,3,4-thiadiazol-2-yl group, and the heterocyclic group may be substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, Q is a heterocyclic group which is a 2-benzothiazolyl group or a 2-benzimidazolyl group, and the heterocyclic group may be substituted with at least one group selected from the group consisting of a halogen atom, a cyano group, a C1-C3 alkyl group and a C1-C3 haloalkyl group;

A carboxamide compound represented by the formula (I) in which $R^3$ is a hydrogen atom or a C1-C3 alkyl group, and Q is a 2-benzimidazolyl group optionally substituted with at least one group selected from the group consisting of a halogen atom, a cyano group, a C1-C3 alkyl group and a C1-C3 haloalkyl group.

A carboxamide compound represented by the formula (I) in which $R^3$ is a hydrogen atom or a C1-C3 alkyl group, and Q is a 2-imidazolyl group, a 4-methyl-2-imidazolyl group, a 4,5-dimethyl-2-imidazolyl group, a 4-chloro-2-imidazolyl group, a 4-bromo-2-imidazolyl group, a 4,5-dicyano-2-imidazolyl group, a 4-fluoro-2-imidazolyl group or a 4-cyano-2-imidazolyl group.

A carboxamide compound represented by the formula (I) in which $R^3$ is a hydrogen atom or a C1-C3 alkyl group, and Q is a 2-benzimidazolyl group, a 4-fluoro-2-benzoimidazolyl group, a 5-fluoro-2-benzimidazolyl group, a 4-chloro-2-benzimidazolyl group, a 5-chloro-2-benzimidazolyl group, a 4-methyl-2-benzimidazolyl group, a 5-methyl-2-benzimidazolyl group, a 5,6-dimethyl-2-benzimidazolyl group, a 5,6-difluoro-2-benzimidazolyl group, a 5,6-dichloro-2-benzimidazolyl group, a 5-trifluoromethyl-2-benzimidazolyl group or a 5-cyano-2-benzimidazolyl group.

A carboxamide compound represented by the formula (I) in which $R^3$ is a hydrogen atom or a C1-C3 alkyl group, and Q is a 2-thiazolyl group, a 4-methyl-2-thiazolyl group, a 4,5-dimethyl-2-thiazolyl group, a 4-chloro-2-thiazolyl group, a 4-bromo-2-thiazolyl group, a 4,5-dicyano-2-thiazolyl group, a 4-fluoro-2-thiazolyl group or a 4-cyano-2-thiazolyl group.

A carboxamide compound represented by the formula (I) in which $R^3$ is a hydrogen atom or a C1-C3 alkyl group, Q is a 2-benzothiazolyl group, a 4-fluoro-2-benzothiazolyl group, a 5-fluoro-2-benzothiazolyl group, a 6-fluoro-2-benzothiazolyl group, a 7-fluoro-2-benzothiazolyl group, 4-chloro-2-benzothiazolyl group, a 5-chloro-2-benzothiazolyl group, a 6-chloro-2-benzothiazolyl group, a 7-chloro-2-benzothiazolyl group, a 4-methyl-2-benzothiazolyl group, a 5-methyl-2-benzothiazolyl group, a 6-methyl-2-benzothiazolyl group, a 7-methyl-2-benzothiazolyl group, a 5,6-dimethyl-2-benzothiazolyl group, a 5,6-difluoro-2-benzothiazolyl group, a 5,6-dichloro-2-benzothiazolyl group, a 5-trifluoromethyl-2-benzothiazolyl group or a 5-cyano-2-benzothiazolyl group.

A carboxamide compound represented by the formula (I) in which $R^3$ is a hydrogen atom or a C1-C3 alkyl group, and Q is a 1,2,4-thiadiazol-5-yl group, a 3-methyl-1,2,4-thiadiazol-5-yl group, a 3-trifluoromethyl-1,2,4-thiadiazol-5-yl group or a 3-cyano-1,2,4-thiadiazol-5-yl group.

A carboxamide compound represented by the formula (I) in which $R^3$ is a hydrogen atom or a C1-C3 alkyl group, and Q is a 1,3,4-thiadiazol-2-yl group, a 5-methyl-1,3,4-thiadiazol-2-yl group, a 5-trifluoromethyl-1,3,4-thiadiazol-2-yl group or a 5-cyano-1,3,4-thiadiazol-2-yl group.

A carboxamide compound represented by the formula (I) in which $R^2$ is a hydrogen atom and $R^3$ is a hydrogen atom.

A carboxamide compound represented by the formula (I) in which $R^2$ is a methyl group and $R^3$ is a hydrogen atom.

A carboxamide compound represented by the formula (I) in which $R^2$ is a hydrogen atom and $R^3$ is a methyl group.

A carboxamide compound represented by the formula (I) in which $R^1$ is a methyl group, $R^2$ is a hydrogen atom, and $R^3$ is a hydrogen atom.

A carboxamide compound represented by the formula (I) in which $R^1$ is a methyl group, $R^2$ is a methyl group, and $R^3$ is a hydrogen atom.

A carboxamide compound represented by the formula (I) in which $R^1$ is a methyl group, $R^2$ is a hydrogen atom, and $R^3$ is a methyl group.

A carboxamide compound represented by the formula (I) in which $R^1$ and $R^2$ bind to each other at an end to form a trimethylene group, and $R^3$ is a hydrogen atom.

A carboxamide compound represented by the formula (I-100):

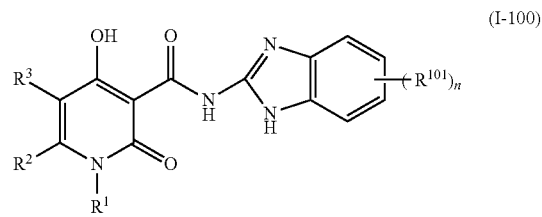

(I-100)

(wherein, $R^1$ represents a C1-C3 alkyl group or C2-C5 alkoxyalkyl group, $R^2$ represents a hydrogen atom or a C1-C3 alkyl group, or $R^1$ and $R^2$ bind to each other at an end to represent a C3-C4 alkylene group, $R^3$ represents a hydrogen atom, a halogen atom or a C1-C3 alkyl group, $R^{100}$ represents a halogen atom, a cyano group, a C1-C3 alkyl group or a C1-C3 haloalkyl group, and n represents an integer of 0 to 4).

A carboxamide compound represented by the formula (I-101):

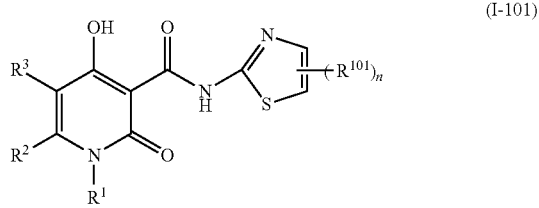
(I-101)

(wherein, $R^1$ represents a C1-C3 alkyl group or a C2-C5 alkoxyalkyl group, $R^2$ represents a hydrogen atom or a C1-C3 alkyl group, or $R^1$ and $R^2$ bind to each other at an end to represent a C3-C4 alkylene group, $R^3$ represents a hydrogen atom, a halogen atom or a C1-C3 alkyl group, $R^{101}$ represents a halogen atom, a cyano group, a C1-C3 alkyl group or a C1-C3 haloalkyl group, and n represents an integer of 0 to 2).

Next, a process for preparing the present compound will be explained. The present compound can be prepared, for example, according to the following (Process A), (Process B) and (Process C).

In the following (Process A), (Process B), (Process C), and Reference Process, if necessary, a protecting group for protecting a particular functional group may be used, and the protecting group can be deprotected under the suitable condition.

(Process A)

The present compound can be prepared by reacting a compound represented by the formula (II) and a compound represented by the formula (III).

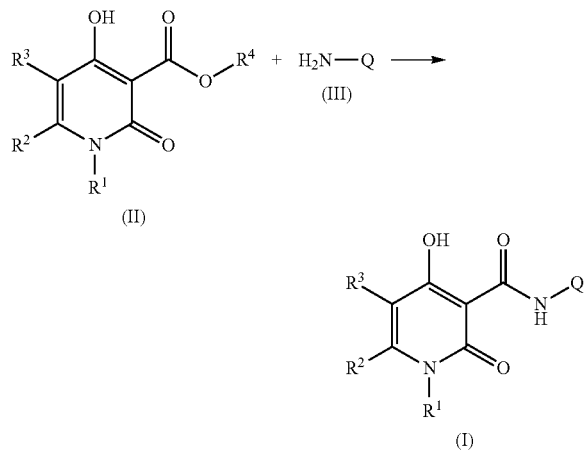

[wherein Q represents a nitrogen-containing 6-membered aromatic heterocyclic group optionally fused with a benzene ring, one of ring constitutional atoms of the heterocyclic group is a nitrogen atom, and the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end to represent a C3-C4 alkylene group, $R^3$ represents a hydrogen atom, a halogen atom or a C1-C3 alkyl group, and $R^4$ represents a C1-C10 alkyl group.]

The reaction is performed usually in the presence of a solvent. If necessary, the reaction may be performed while a C1-C10 alcohol produced accompanying with progression of the reaction is removed by adsorption, distillation or azeotropy or the like.

Examples of the solvent to be used in the reaction include halogenated aromatic hydrocarbons such as chlorobenzene, bromobenzene and the like, aromatic hydrocarbons such as toluene, xylene and the like, acid amides such as N,N-dimethylformamide and the like, and a mixture thereof.

At the reaction, the compound represented by the formula (II) is usually used at a ratio of 0.1 to 5 moles per 1 mole of the compound represented by the formula (III).

A reaction temperature in the reaction is usually in a range of 80 to 180° C., and a reaction time is usually in a range of 0.1 to 24 hours.

After completion of the reaction, the present compound represented by the formula (I) can be isolated, for example, by performing the following post-treatment procedure. The reaction mixture is cooled to room temperature, the resulting solid is collected by filtration, and the solid is washed with an organic solvent and dried;

the reaction mixture is concentrated under reduced pressure, and the resulting solid is further washed with an organic solvent and dried.

The isolated present compound represented by the formula (I) may also be further purified by a procedure such as chromatography, recrystallization and the like.

(Process B)

The present compound can be prepared by reacting a compound represented by the formula (XIII) and a compound represented by the formula (III) using carbonyldiimidazole.

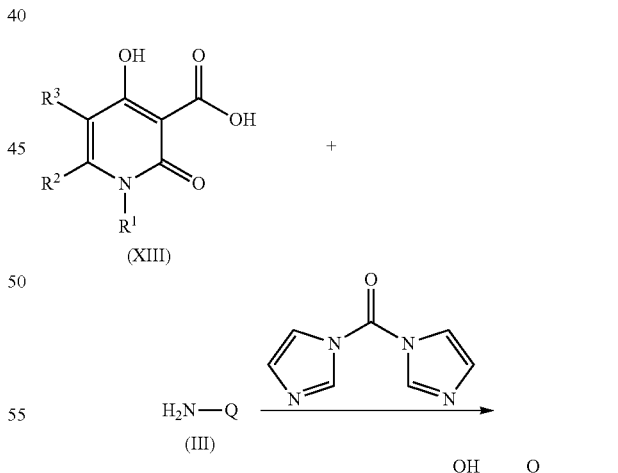

[wherein $R^1$, $R^2$, $R^3$ and Q are as defined above.]

The reaction is performed usually in the presence of a solvent. Examples of the solvent used in the reaction include nitriles such as acetonitrile, propionitrile and the like, ethers such as diethyl ether, t-butyl methyl ether, tetrahydrofuran, 1,4-dioxane and the like, aromatic hydrocarbons such as toluene, xylene and the like, acid amides such as N,N-dimethylformamide and the like, and a mixture thereof.

At the reaction, the compound represented by the formula (III) is usually used at a ratio of 0.1 to 5 moles per 1 mole of the compound represented by the formula (XIII). Carbonyldiimidazole is usually used at a ratio of 0.1 to 5 moles per 1 mole of the compound represented by the formula (XIII).

A reaction temperature in the reaction is usually in a range of −10 to 150° C., and a reaction time is usually in a range of 0.1 to 24 hours.

After completion of the reaction, the present compound represented by the formula (I) can be isolated by performing a post-treatment procedure such as the resulting solid being collected by filtration, washing the solid with an organic solvent, drying it and so on. The isolated present compound represented by the formula (I) may also be further purified by a procedure such as chromatography, recrystallization and the like.

(Process C)

The present compound can be prepared by reacting a compound represented by the formula (XIII) and a compound represented by the formula (XV) in the presence of alkaline earth metal triflate such as magnesium triflate, calcium triflate and the like.

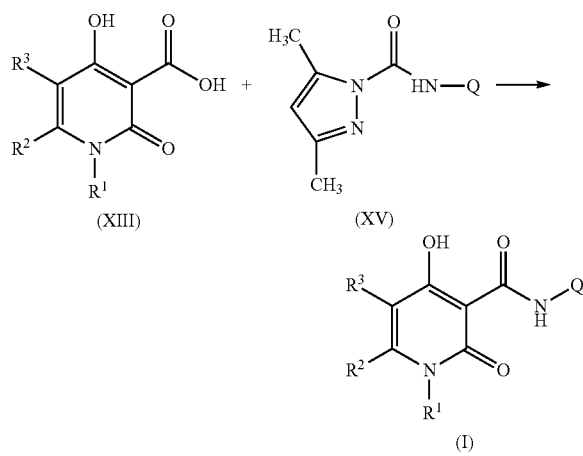

[wherein $R^1$, $R^2$, $R^3$ and Q are as defined above.]

The reaction is performed usually in the presence of a solvent. Examples of the solvent used in the reaction include aromatic hydrocarbons such as toluene, xylene and the like.

At the reaction, the compound represented by the formula (XV) is usually used at a ratio of 1 mole per 1 mole of the compound represented by the formula (XIII), and the alkaline earth metal triflate is usually used at a ratio of 0.01 to 0.1 moles per 1 mole of the compound represented by the formula (XIII).

A reaction temperature in the reaction is usually in a range of 100 to 150° C. and the reaction time is usually in a range of 0.1 to 24 hours.

After completion of the reaction, the compound represented by the formula (I) can be isolated by performing a post-treatment procedure such as the reaction mixture being cooled, the resulting solid being collected by filtration, washing the solid with an organic solvent, drying it and so on. The isolated compound represented by the formula (I) may also be further purified by a procedure such as chromatography, recrystallization and the like.

The compound represented by the formula (XV) can be prepared from a compound represented by the formula (XVI):

and 3,5-dimethylimidazole.

Next, a process for preparing an intermediate for preparing the present compound will be explained as Reference Process.

(Reference Process 1)

A compound represented by the formula (II-1) among the compounds represented by the formula (II) can be prepared from a compound represented by the formula (IV) according to the following scheme.

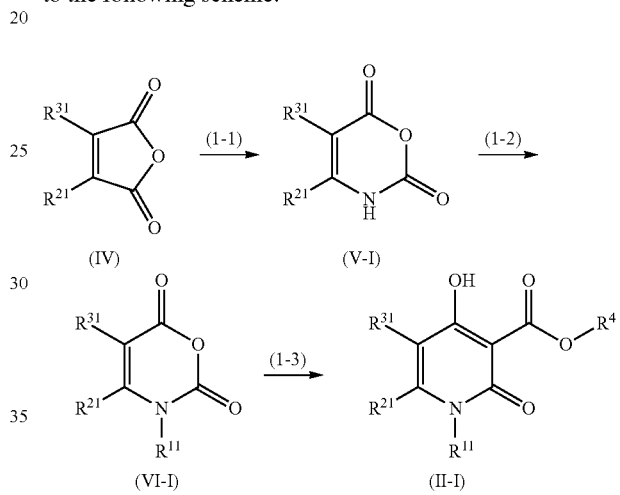

[wherein Q is as defined, above, $R^{11}$ represents a C1-C3 alkyl group or a C2-C5 alkoxyalkyl group, $R^{21}$ represents a hydrogen atom or a C1-C3 alkyl group, $R^{31}$ represents a hydrogen atom or a C1-C3 alkyl group, and $R^4$ represents a C1-C10 alkyl group]

Step (1-1)

A compound represented by the formula (V-1) can be prepared by reacting a compound represented by the formula (IV) with an azide compound (e.g. sodium azide, and trimethylsilyl azide), and further reacting the resulting product with an alcohol compound (e.g. methanol, and ethanol).

The reaction is performed usually in the presence of a solvent. Examples of the solvent used in the reaction include halogenated hydrocarbons such as chloroform, carbon tetrachloride and the like, halogenated aromatic hydrocarbons such as chlorobenzene, bromobenzene and the like, aromatic hydrocarbons such as toluene, xylene and the like, acid amides such as N,N-dimethylformamide and the like and a mixture thereof.

At the reaction, the azide compound is usually used at a ratio of 1 to 5 moles per 1 mole of the compound represented by the formula (IV), and the alcohol compound is usually used at a ratio of 1 mole per 1 mole of the azide compound.

When the compound represented by the formula (IV) is reacted with the azide compound, a reaction temperature is usually in a range of −20 to 100° C., and a reaction time is usually in a range of 0.1 to 24 hours. When the resulting product is reacted with the alcohol compound, a reaction temperature is usually in a range of −20 to 10° C., and a reaction time is usually in a range of 0.1 to 24 hours.

After completion of the reaction, the compound represented by the formula (V-1) can be isolated by performing a post-treatment procedure such as a solid produced in the reaction mixture being collected by filtration, washing the solid with an organic solvent, drying it and so on. The isolated compound represented by the formula (V-1) can be further purified by a procedure such as chromatography, recrystallization and the like.

Alternatively, the compound represented by the formula (V-1) can be also prepared by the method shown in Tetrahedron Letters No. 4, pp. 243-246, 1976.

Step (1-2)

A compound represented by the formula (VI-1) can be prepared by reacting a compound represented by the formula (V-1) with a compound represented by the formula (X):

$$R^{11}\text{—}X \quad (X)$$

[wherein $R^{11}$ is as defined above, and X represents a leaving group such as a halogen atom (e.g. chlorine atom, bromine atom and iodine atom), a sulfonyloxy group (e.g. methanesulfonyloxy group, methoxysulfonyloxy group, and p-toluenesulfonyloxy group) and the like] in the presence of a base.

The reaction is usually performed in the presence of a solvent. Examples of the solvent used in the reaction include ketones such as acetone, ethyl methyl ketone and the like, halogenated aromatic hydrocarbons such as chlorobenzene, bromobenzene and the like, aromatic hydrocarbons such as toluene, xylene and the like, acid amides such as N,N-dimethylformamide and the like, ethers such as tetrahydrofuran, 1,4-dioxane and the like, nitriles such as acetonitrile and the like, and a mixture thereof.

Examples of the compound represented by the formula (X) which is used in the reaction include methyl iodide, methyl bromide, dimethyl sulfate, ethyl iodide, propyl iodide, and chloromethyl ethyl ether.

Examples of the base used in the reaction include carbonates such as potassium carbonate, cesium carbonate and the like, and alkali metal hydrides such as sodium hydride, potassium hydride and the like.

At the reaction, the compound represented by the formula (X) is usually used at a ratio of 1 to 5 moles per 1 mole of the compound represented by the formula (VI-1), and the base is usually used at a ratio of 1 to 5 moles per 1 mole of the compound represented by the formula (VI-1).

A reaction temperature in the reaction is usually in a range of −20 to 150° C., and a reaction time is usually in a range of 0.1 to 24 hours.

After completion of the reaction, the compound represented by the formula (VI-1) can be isolated by performing the following post-treatment procedure.

The reaction mixture is cooled to room temperature and filtered, the filtrate is concentrated under reduced pressure, and the resulting solid is washed with an organic solvent and dried;
water is added to the reaction mixture, this is extracted with an organic solvent and the organic layer is concentrated.

The isolated compound represented by the formula (VI-1) may also be further purified by a procedure such as chromatography, recrystallization and the like.

Step (1-3)

A compound represented by the formula (II-1) can be prepared by reacting a compound represented by the formula (VI-1) with dialkyl malonate represented by the formula:

$$CH_2(COOR^4)_2$$

(wherein $R^4$ is as defined above)
in the presence of a base.

The reaction is usually performed in the presence of a solvent. Examples of the solvent used in the reaction include ethers such as tetrahydrofuran, 1,4-dioxane and the like, halogenated aromatic hydrocarbons such as chlorobenzene, bromobenzene and the like, aromatic hydrocarbons such as toluene, xylene and the like, acid amides such as N,N-dimethylformamide and the like, and a mixture thereof.

Examples of the dialkyl malonate represented by the formula $CH_2(COOR^4)_2$ used in the reaction include dimethyl malonate and diethyl malonate.

Examples of the base used in reaction include: metal alkoxides represented by the formula:

$$NaOR^4$$

(wherein $R^4$ is as defined above) and
alkali metal hydrides such as sodium hydride, potassium hydride and the like.

At the reaction, dialkyl malonate is usually used at a ratio of 1 to 5 moles per 1 mole of the compound represented by the formula (VI-1), and the base is usually used at a ratio of 1 to 5 moles per 1 mole of the compound represented by the formula (VI-1).

A reaction temperature in the reaction is usually in a range of −10 to 150° C., and a reaction time is usually in a range of 0.1 to 24 hours.

After completion of the reaction, the compound represented by the formula (II-1) can be isolated by performing a post-treatment procedure such as the reaction mixture being cooled to room temperature, adding acidic water such as dilute hydrochloric acid and the like to the reaction mixture to make the aqueous layer acidic, extracting this with an organic solvent, drying and concentrating the organic layer, and so on. The isolated compound represented by the formula (II-1) may also be further purified by a procedure such as chromatography, recrystallization and the like.

In addition, a compound represented by the formula (II-2) among the compound represented by the formula (II) can be prepared, for example, according to the following scheme:

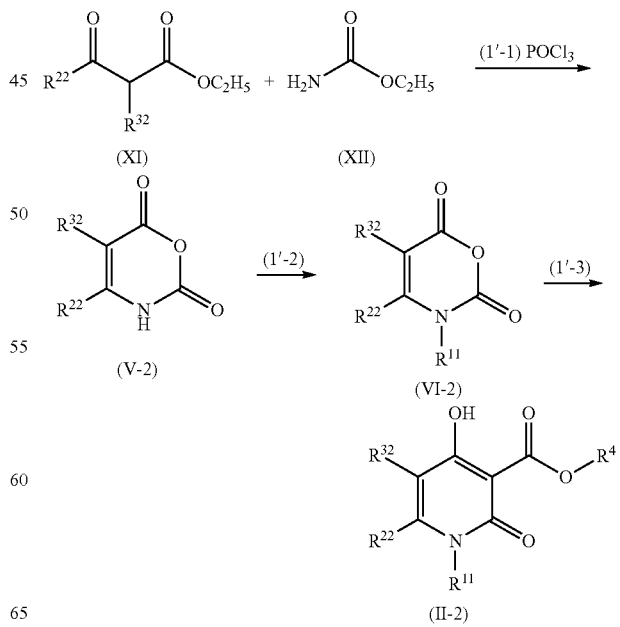

[wherein, Q, $R^{11}$ and $R^4$ are as defined above, $R^{22}$ represents a C1-C3 alkyl group, $R^{32}$ represents a halogen atom, and $R^4$ represents a C1-C10 alkyl group.]

Step (1'-1)

A compound represented by the formula (V-2) can be prepared according to the method described in Tetrahedron Letters No. 4, pp 243-246, 1976.

A step (1'-2) and a step (1'-3) are performed as in the step (1-2) and the step (1-3).

(Reference Process 2)

The compound represented by the formula (II) can also be prepared according to the following scheme:

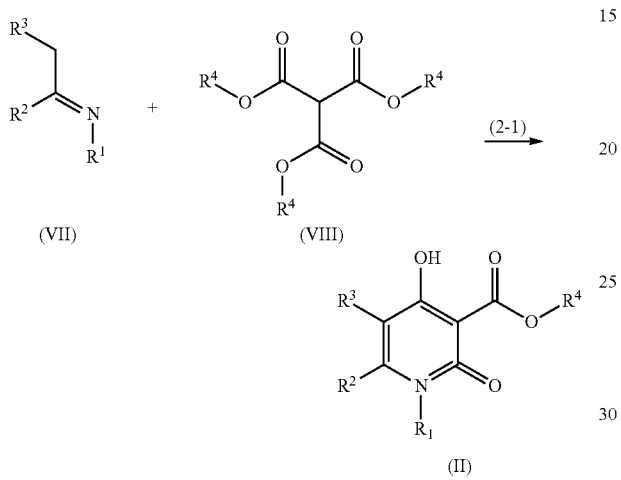

[wherein $R^1$, $R^2$, $R^3$, $R^4$ and Q are as defined above.]

Step (2-1)

The compound represented by the formula (II) can be prepared by reacting a compound represented by the formula (VII) with a compound represented by the formula (VIII).

The reaction can be performed usually in the absence of a solvent. Alternatively, the reaction may be performed in the presence of a solvent while an alcohol compound produced accompanying a reaction is removed by azeotropy and the like. Examples of the solvent used in the reaction include halogenated aromatic hydrocarbons such as chlorobenzene, bromobenzene and the like, aromatic hydrocarbons such as toluene, xylene and the like, acid amides such as N,N-dimethylformamide and the like, and a mixture thereof.

At the reaction, the compound represented by the formula (VIII) is usually used at a ratio of 1 to 50 moles per 1 mole of the compound represented by the formula (VII).

A reaction temperature in the reaction is usually in a range of 100 to 250° C., and a reaction time is usually in a range of 0.1 to 24 hours.

After completion of the reaction, the compound represented by the formula (II) can be isolated, for example, by performing the following post-treatment procedure.

The reaction mixture is cooled to room temperature, the resulting solid is filtered, and the solid is washed with an organic solvent and dried;
after the reaction mixture is cooled to room temperature, water is added to the reaction mixture, this is extracted with an organic solvent, and the organic layer is concentrated.

The isolated compound represented by the formula (II) may also be further purified by a procedure such as chromatography, recrystallization and the like.

(Reference Process 3)

Among the compound represented by the formula (XIII), a compound represented by the formula (XIII-1) can be prepared from a compound represented by the formula (XVII) according to the following scheme:

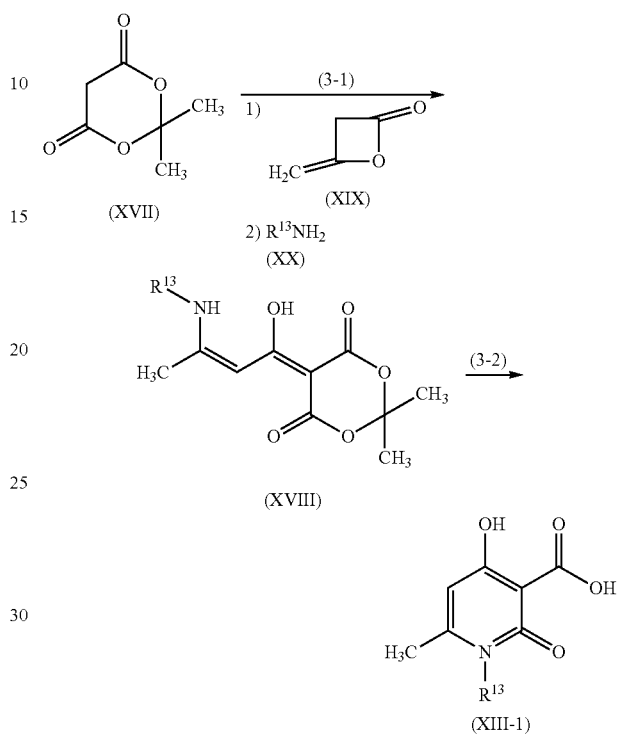

[wherein $R^{13}$ represents a C1-C3 alkyl group.]

(Step 3-1)

A compound represented by the formula (XVIII) can be prepared by reacting a compound represented by the formula (XVII) with diketene represented by the formula (XIX) in the presence of tertiary amine or pyridines (first stage), and reacting the resulting product with a compound represented by the formula (XX) (second stage).

Each reaction is usually performed in the presence of a solvent. Examples of the solvent used in the reaction include nitriles such as acetonitrile, propionitrile and the like, ethers such as diethyl ether, t-butyl methyl ether, tetrahydrofuran, 1,4-dioxane and the like, halogenated aromatic hydrocarbons such as chlorobenzene, bromobenzene and the like, aromatic hydrocarbons such as toluene, xylene and the like, and a mixture thereof.

In the reaction at the first stage, diketene represented by the formula (XIX) is usually used at a ratio of 1 mole per 1 mole of the compound represented by the formula (XVII).

In the reaction at the first stage, examples of the tertiary amine used include triethylamine and tri-n-propylamine; examples of pyridines include pyridine and 4-dimethylaminopyridine. In the reaction at the first stage, tertiary amine or pyridines is usually used at a ratio of 1 mole per 1 mole of the compound represented by the formula (XVII).

A reaction temperature at the first stage is usually in a range of 0 to 40° C., and a reaction time is usually in a range of 0.1 to 24 hours.

The reaction mixture obtained by the reaction at the first stage is usually used as it is in the reaction at the second stage.

The reaction at the second stage is usually performed by mixing the reaction mixture obtained at the first stage and a compound represented by the formula (XX).

In the reaction at the second stage, the compound represented by the formula (XX) is usually used at a ratio of 2 mole per 1 mole of the compound represented by the formula (XVII).

A reaction temperature in the reaction at the second stage is usually in a range of 0 to 40° C., and a reaction time is usually in a range of 0.1 to 24 hours.

After completion of the reaction at the second stage, the compound represented by the formula (XVIII) can be isolated by performing a post-treatment procedure such as by adding acid (e.g. dilute hydrochloric acid, dilute sulfuric acid) to the reaction mixture, collecting the resulting crystal by filtration, drying it and so on. The isolated compound represented by the formula (XVIII) may also be further purified by a procedure such as chromatography, recrystallization and the like.

(Step 3-2)

A compound represented by the formula (XIII-1) can be prepared by retaining a compound represented by the formula (XVIII) at 40 to 120° C. for 0.1 to 24 hours.

The procedure is usually performed in the presence of a solvent. Examples of the solvent used in the procedure include nitriles such as acetonitrile, propionitrile and the like, ethers such as t-butyl methyl ether, tetrahydrofuran, 1,4-dioxane and the like, halogenated aromatic hydrocarbons such as chlorobenzene, bromobenzene and the like, aromatic hydrocarbons such as toluene, xylene and the like, and a mixture thereof.

After disappearance of the compound represented by the formula (XVIII) is confirmed by an analysis means such as thin layer chromatography and the like, the compound represented by the formula (XIII-1) can be isolated by performing a post-treatment procedure such as addition of the resulting mixture to water, extraction with an organic solvent, concentration of an organic layer and the like. The isolated compound represented by the formula (XIII-1) may also be further purified by a procedure such as chromatography, recrystallization and the like.

(Reference Process 4)

Among the compound represented by the formula (XIII), a compound represented by the formula (XIII-2) can be prepared by reacting a compound represented by the formula (XVIII) with a halogenating agent at −10 to 30° C. (first stage) and retaining the resulting product at 40 to 120° C. for 0.1 to 24 hours (second stage):

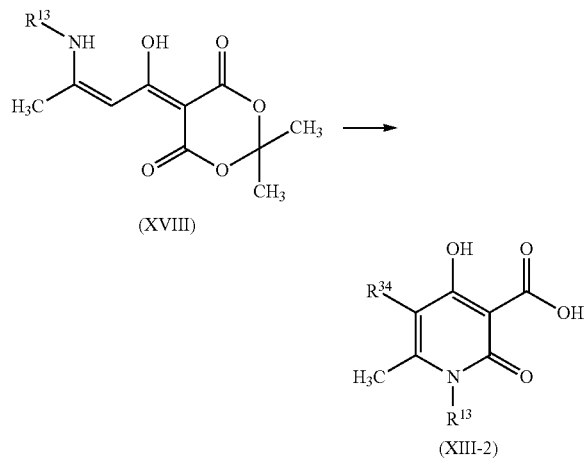

(XVIII)

(XIII-2)

[wherein $R^{34}$ represents a halogen atom, and $R^{13}$ is as defined above.]

The reaction at the first stage is usually performed in the presence of a solvent. Examples of the solvent used in the reaction include nitriles such as acetonitrile, propionitrile and the like, ethers such as diethyl ether, t-butyl methyl ether, tetrahydrofuran, 1,4-dioxane and the like, halogenated aromatic hydrocarbons such as chlorobenzene and bromobenzene and the like, aromatic hydrocarbons such as toluene, xylene and the like, and a mixture thereof.

Examples of the halogenating agent used in the reaction at the first stage include N-fruoropyridinium salt such as N,N'-difluoro-2,2'-bipyridinium bis(tetrafluoroborate) and the like, and N-halogenosuccinimides such as N-chlorosuccinimide, N-bromosuccinimide, N-iodosuccinimide and the like.

At the reaction, the halogenating agent is usually used at a ratio of 0.5 to 2 moles per 1 mole of the compound represented by the formula (XVIII).

A reaction temperature at the first stage is usually in a range of −10 to 30° C., and a reaction time is usually in a range of 0.1 to 5 hours.

The reaction mixture obtained in the reaction at the first stage can be usually used as it is in a procedure at the second stage.

The procedure at the second stage is usually performed by retaining the reaction mixture obtained in the first stage at 40 to 120° C.

Thereafter, the compound represented by the formula (XIII-2) can be isolated by performing a post-treatment procedure, such as addition of the reaction mixture to water, extraction with an organic solvent, concentration of the organic layer and the like. The isolated compound represented by the formula (XIII-2) may also be further purified by a procedure such as chromatography, recrystallization and the like.

A compound represented by the formula (III) can be purchased commercially or prepared according to the method described in, for example, Indian Journal of Chemistry, Section B: Organic Chemistry Including Medicinal Chemistry (1998), 37B(1), 84 p, Bioorganic & Medicinal Chemistry Letters (2002), 12(16), 2221-2224 p, JP-B No. 52-009736, Journal of Organic Chemistry (1994), 59(24), 7299-7305 p, Phosphorus, Sulfur and Silicon and the Related Elements (2002), 177(11), 2651-2659 p, Bioorganic & Medicinal Chemistry (2001), 9(12), 3231-3241, Chemische Berichte (1960), 93, 2190-2097 p, "The Chemistry of Heterocyclic Compounds" (John Wiley & Sons, Inc.) and so on.

A compound represented by the formula (IV), a compound represented by the formula (VII), a compound represented by the formula (VIII), a compound represented by the formula (X) and dialkyl malonate can be purchased commercially or prepared according to the known methods.

Examples of a plant disease which can be controlled by the present compound include the following diseases:

*Pyricularia oryzae* and *Cochliobolus miyabeanus* and *Rhizoctonia solani* of rice;

*Erysiphe graminis, Gibberella zeae, Fusarium graminearum, Fusarium culmorum, F. avenaceum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Gaeumanomyces graminis*, of wheat and barley;

*Diaporthe citri, Elsinoe fawcetti, Penicillium digitatum* and *P. italicum* of citrus;

*Sclerotinia mali, Valsa mali, Podosphaera leucotricha, Alternaria mali* and *Venturia inaequalis* of apple;

*Venturia nashicola, V. pirina, Alternaria kikuchiana* and *Gymnosporangium haraeanum* of pear;

*Sclerotinia cinerea, Cladosporium carpophilum* and *Phomopsis* sp. of peach; *Elsinoe ampelina, Glomerella cingulata, Uncinula necator, Phakopsora ampelopsidis, Guignardia bidwellii* and *Plasmopara viticola*, of grape;
*Gloeosporium kaki, Cercospora kaki* and *Mycosphaerella nawae* of Japanese persimmon;
*Colletotrichum lagenarium, Sphaerotheca fuliginea, Mycosphaerella melonis, Fusarium oxysporum, Pseudoperonospora cubensis, Phytophthora* sp. and *Pythium* sp. of gourd;
*Alternaria solani, Cladosporium fulvum* and *Phytophthora infestans* of tomato;
*Phomopsis vexans* and *Erysiphe cichoracearum*, of eggplant; *Alternaria japonica* and *Cercosporella brassicae* of Cruciferae vegetables;
*Puccinia allii* of leek; *Cercospora kikuchii, Elsinoe glycines, Diaporthe phaseolorum* var. *sojae* and *Phakospora pachrhizii* of soybean; *Colletotrichum lindemthianum* of kidney bean; *Cercospora personata* and *Cercospora arachidicola* of peanut; *Erysiphe pisi* of pea; *Alternaria solani* and *Phytophthora infestans* of potato; *Sphaerotheca humuli* of strawberry; *Exobasidium reticulatum* and *Elsinoe leucospila* of tea; *Alternaria longipes, Erysiphe cichoracearum, Colletotrichum tabacum, Peronospora tabacina* and *Phytophthora nicotianae* of tobacco; *Cercospora beticola* of sugar beet; *Diplocarpon rosae* and *Sphaerotheca pannosa* of rose; *Septoria chrysanthemi-indici* and *Puccinia horiana* of chrysanthemum; *Botrytis cinerea* and *Sclerotinia sclerotiorum* of various crops; *Sclerotinia homeocarpaa* and *Rhizoctonia solani* of lawn.

The plant disease controlling agent of the present invention may be the present compound itself, but usually, the agent contains the present compound, and an inert carrier such as a solid carrier, a liquid carrier and the like, and is formulated in preparations by further mixing a surfactant, and other adjuvant for preparations. Examples of such the preparations includes emulsifiable concentrates, wettable powders, water dispersible granule, emulsion preparations, flowable preparations, dusts, and granules. These preparations contain the present compound as an active ingredient usually at 0.1 to 90% in terms of ratio by weight.

Examples of the solid carrier used upon formulating the preparations include fine powders and particles of minerals such as kaolin clay, attapulgite clay, bentonite, montmorillonite, acid clay, pyrophyllite, talc, diatomaceous earth, calcite and the like, natural organics such as corncob powders, walnut shell flour and the like, synthetic organics such as urea and the like, salts such as calcium carbonate, ammonium sulfate and the like, synthetic inorganic substances such as synthetic hydrous silicon oxide and the like, and the examples of the liquid carrier include aromatic hydrocarbons such as xylene, alkylbenzene, methylnaphthalene and the like, alcohols such as 2-propanol, ethylene glycol, propylene glycol, ethylene glycol monomethyl ether and the like, ketones such as acetone, cyclohexanone, isophorone and the like, vegetable oils such as soybean oil, cottonseed oil and the like, aliphatic hydrocarbons, esters, dimethyl sulfoxide, acetonitrile, and water.

Examples of the surfactant includes anionic surfactants such as alkylsulfate ester salt, alkylarylsulfonate salt, dialkylsulfosuccinate salt, polyoxyethylene alkyl aryl ether phosphate ester salt, ligninsulfonate salt, naphathalene sulfonate formaldehyde polycondensate and the like, and noinic surfactants such as polyoxyethylene alkyl aryl ether, polyoxyethylene alkyl polyoxypropylene block copolymer, sorbitan fatty acid ester and the like.

Examples of other adjuvant for preparations include water-soluble polymers such as polyvinyl alcohol, polyvinylpyrrolidone and the like, polysaccarides such as gum arabic, alginic acid and a salt thereof, CMC (carboxymethylcellulose), xanthan gum and the like, inorganic substances such as aluminum magnesium silicate, alumina sol and the like, preservative, coloring agent, and stabilizers such as PAP (acidic isopropyl phosphate), BHT and the like.

The plant disease controlling agent of the present invention is used, for example, for protecting a plant against a plant disease by foliage treatment of the plant, or is used for protecting a plant growing on a soil against a plant disease by treating the soil. When the plant disease controlling agent of the present invention is used by foliage-treating a plant, or when the agent is used by treating a soil, the amount of treatment varies depending on a kind of a crop which is a plant to be controlled, a kind of a disease to be controlled, an infestation level of a disease to be controlled, a preparation form, a treating term, weather condition and the like, and the amount in terms of the present compound per 10000 $m^2$ is usually 1 to 5000 g, preferably 5 to 1000 g.

In the case of emulsifiable concentrates, wettable powders, flowable preparations and the like, a plant is usually treated by diluting the agent with water, followed by spraying. A concentration of the present compound is usually in a range of 0.0001 to 3% by weight, preferably in a range of 0.0005 to 1% by weight. In the case of dusts, granules and the like, a plant is treated with the agent without dilution.

Alternatively, the plant disease controlling agent of the present invention may be used by a treating method such as seed disinfection. Examples of the method of disinfecting a seed include a method of immersing a plant seed in a plant disease controlling agent of the present invention which has been prepared so that a concentration of the present compound in adjusted to 1 to 1000 ppm, a method of spraying or applying the plant disease controlling agent of the present invention having a concentration of the present compound 1 to 1000 ppm on plant seeds, and a method of coating plant seeds with the plant disease controlling agent of the present invention which has been formulated into powders.

The plant disease controlling method of the present invention is usually performed by treating a plant which is expected to develop a disease or a soil where the plant grows, and/or treating a plant which is confirmed to have developed a disease or a soil where the plant grows with an effective amount of the plant disease controlling agent of the present invention.

The plant disease controlling agent of the present invention is usually used as a plant disease controlling agent for horticulture, i.e., a plant disease controlling agent for controlling a plant disease in plowed field, paddy, orchard, tea garden, meadow, lawn and so on.

The plant disease controlling agent of the present invention may be used (mixed or combined) in conjunction with other fungicides, insecticides, acaricides, nematicides, herbicides, plant growth controlling agents and/or fertilizers.

Examples of an active ingredient of such other fungicides include chlorothalonil, fluazinam, dichlofluanid, fosetyl-Al, cyclic imido derivatives (captan, captafol, folpet etc.), dithiocarbamate derivatives (maneb, mancozeb, thiram, ziram, zineb, propineb etc.), inorganic or organic copper derivatives (basic copper sulfate, copper oxychloride, copper hydroxide, oxine-copper etc.), acylalanine derivatives (metalaxyl, furalaxyl, ofurace, cyprofuram, benalaxyl, oxadixyl etc.), strobilurin compounds (kresoxim-methyl, azoxystrobin, trifloxystrobin, picoxystrobin, pyraciostrobin, dimoxystrobin, fluoxastrobin, metominostrobin etc.), anilinopyrimidine derivatives (cyprodinil, pyrimethanil, mepanipyrim etc.), phenylpyrrole derivatives (fenpiclonil, fludioxonil etc.), imide derivatives (procymidone, iprodione, vincrozolin etc.), benzimidazole derivatives (carbendazim, benomyl, thiabendazol, thiophanate-methyl etc.), amine derivatives (fenpropimorph, tridemorph, fenpropidin, spiroxamine etc.), azole derivatives (propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol etc.), cymoxanil, dimethomorph, famoxadone, fenamidone, iprovalicarb, benthiavalicarb, cyazofamid, picobenzamid, mandipropamide, zoxamide, ethaboxam, boscalid, pyribencarb, fluopicolide, fenhexamid, quinoxyfen, proquinazid, diethofencarb, acibenzolar-S-methyl, guazatine and penthiopyrad.

Specific examples of the present compound include the following compounds.

Carboxamide compounds represented by the following formulae (i) to (xxviii):

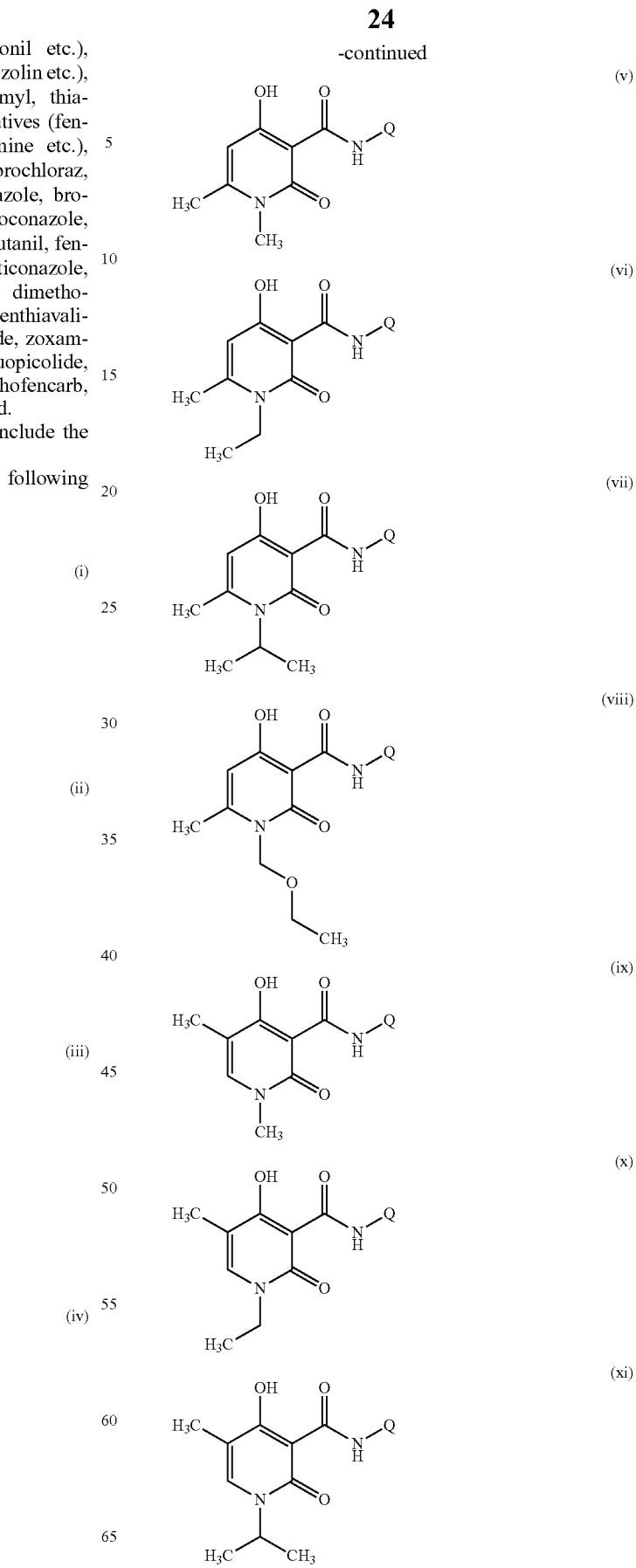

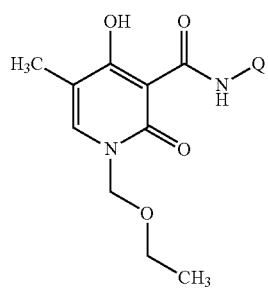
(xii)
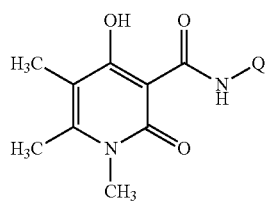
(xiii)
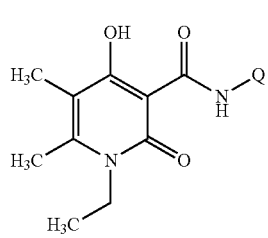
(xiv)
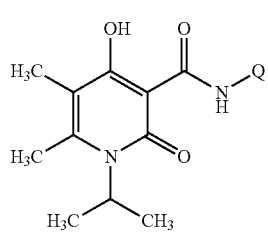
(xv)
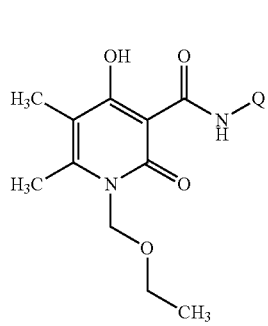
(xvi)
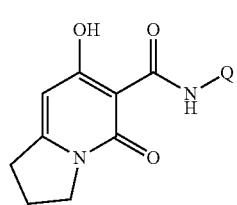
(xvii)

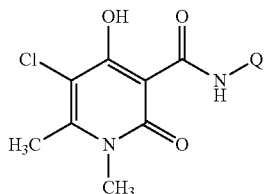

(xxv)

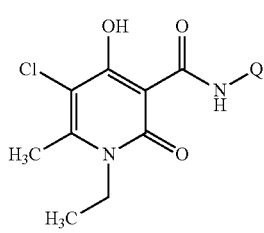

(xxvi)

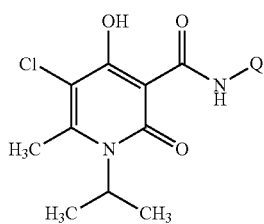

(xxvii)

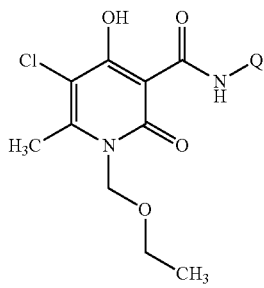

(xxviii)

In the formulae (i) to (xxviii), Q represents any one of the following groups.

2-imidazolyl group, 4-methyl-2-imidazolyl group, 4,5-dimethyl-2-imidazolyl group, 4-chloro-2-imidazolyl group, 4-bromo-2-imidazolyl group, 4,5-dicyano-2-imidazolyl group, 4-fluoro-2-imidazolyl group, 4-cyano-2-imidazolyl group, 2-benzimidazolyl group, 4-fluoro-2-benzimidazolyl group, 5-fluoro-2-benzimidazolyl group, 4-chloro-2-benzimidazolyl group, 5-chloro-2-benzimidazolyl group, 4-cyano-2-benzimidazolyl group, 5-cyano-2-benzimidazolyl group, 4-methyl-2-benzimidazolyl group, 5-methyl-2-benzimidazolyl group, 4-trifluoromethyl-2-benzimidazolyl group, 5-trifluoromethyl-2-benzimidazolyl group, 5,6-dimethyl-2-benzimidazolyl group, 5,6-difluoro-2-benzimidazolyl group, 5,6-dichloro-2-benzimidazolyl group, 5-trifluoromethyl-2-benzimidazolyl group, 5-cyano-2-benzimidazolyl group, 2-thiazolyl group, 4-methyl-2-thiazolyl group, 4,5-dimethyl-2-thiazolyl group, 4-chloro-2-thiazolyl group, 4-bromo-2-thiazolyl group, 4,5-dicyano-2-thiazolyl group, 4-fluoro-2-thiazolyl group, 4-cyano-2-thiazolyl group, 2-benzothiazolyl group, 4-fluoro-2-benzothiazolyl group, 5-fluoro-2-benzothiazolyl group, 6-fluoro-2-benzothiazolyl group, 7-fluoro-2-benzothiazolyl group, 4-chloro-2-benzothiazolyl group, 5-chloro-2-benzothiazolyl group, 6-chloro-2-benzothiazolyl group, 7-chloro-2-benzothiazolyl group, 4-methyl-2-benzothiazolyl group, 5-methyl-2-benzothiazolyl group, 6-methyl-2-benzothiazolyl group, 7-methyl-2-benzothiazolyl group, 5,6-dimethyl-2-benzothiazolyl group, 5,6-difluoro-2-benzothiazolyl group, 5,6-dichloro-2-benzothiazolyl group, 5-trifluoromethyl-2-benzothiazolyl group, 5-cyano-2-benzothiazolyl group, 3-pyrazolyl group, 1-methyl-3-pyrazolyl group, 1,5-dimethyl-3-pyrazolyl group, 4-chloro-1-methyl-3-pyrazolyl group, 1-ethyl-3-pyrazolyl group, 1-(2,2,2-trifluoroethyl)-3-pyrazolyl group, 1,2,4-thiadiazol-5-yl group, 3-methyl-1,2,4-thiadiazol-5-yl group, 3-trifluoromethyl-1,2,4-thiadiazol-5-yl group, 3-cyano-1,2,4-thiadiazol-5-yl group, 1,3,4-thiadiazol-2-yl group, 5-methyl-1,3,4-thiadiazol-2-yl group, 5-trifluoromethyl-1,3,4-thiadiazol-2-yl group and 5-cyano-1,3,4-thiadiazol-2-yl group.

Embodiments of intermediates of the present compound include, for example, the following compounds.

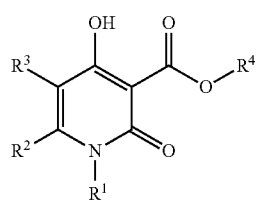

(II)

A compound represented by the formula (II) in which $R^1$ is a C1-C3 alkyl group or C2-C5 alkoxyalkyl group, $R^2$ is a hydrogen atom or C1-C3 alkyl group, and $R^3$ is a hydrogen atom, halogen atom or C1-C3 alkyl group.

A compound represented by the formula (II) in which $R^1$ and $R^2$ bind to each other at an end to form a C3-C4 alkylene group, and $R^3$ is a hydrogen atom, halogen atom or C1-C3 alkyl group.

A compound represented by the formula (II) in which $R^1$ is a C1-C3 alkyl group, $R^2$ is a hydrogen atom or C1-C3 alkyl group, and $R^3$ is a hydrogen atom or C1-C3 alkyl group.

A compound represented by the formula (II) in which $R^1$ is a C1-C3 alkyl group, $R^2$ is a hydrogen atom or C1-C3 alkyl group, and $R^3$ is a halogen atom.

A compound represented by the formula (II) in which $R^1$ is a C1-C3 alkyl group, $R^2$ is a hydrogen atom or C1-C3 alkyl group, and $R^3$ is a fluorine atom.

A compound represented by the formula (II) in which $R^1$ is a C1-C3 alkyl group, $R^2$ is a C1-C3 alkyl group, and $R^3$ is a fluorine atom.

A compound represented by the formula (II) in which $R^1$ is a C1-C3 alkyl group, $R^2$ is a methyl group, and $R^3$ is a fluorine atom.

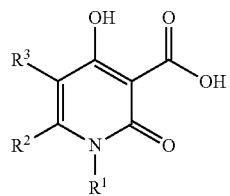

(XIII)

A compound represented by the formula (XIII) in which $R^1$ is a C1-C3 alkyl group or C2-C5 alkoxyalkyl group, $R^2$ is a hydrogen atom or C1-C3 alkyl group, and $R^3$ is a hydrogen atom, halogen atom or C1-C3 alkyl group.

A compound represented by the formula (XIII) in which $R^1$ and $R^2$ bind to each other at an end to form a C3-C4 alkylene group, and $R^3$ is a hydrogen atom, halogen atom or C1-C3 alkyl group.

A compound represented by the formula (XIII) in which $R^1$ is a C1-C3 alkyl group, $R^2$ is a hydrogen atom or C1-C3 alkyl group, and $R^3$ is a hydrogen atom or C1-C3 alkyl group.

A compound represented by the formula (XIII) in which $R^1$ is a C1-C3 alkyl group, $R^2$ is a hydrogen atom or C1-C3 alkyl group, and $R^3$ is a halogen atom.

A compound represented by the formula (XIII) in which $R^1$ is a C1-C3 alkyl group, $R^2$ is a hydrogen atom or C1-C3 alkyl group, and $R^3$ is a fluorine atom.

A compound represented by the formula (XIII) in which $R^1$ is a C1-C3 alkyl group, $R^2$ is a C1-C3 alkyl group, and $R^3$ is a fluorine atom.

A compound represented by the formula (XIII) in which $R^1$ is a C1-C3 alkyl group, $R^2$ is a methyl group, and $R^3$ is a halogen atom.

A compound represented by the formula (XIII) in which $R^1$ is a C1-C3 alkyl group, $R^2$ is a methyl group, and $R^3$ is a fluorine atom.

EXAMPLES

The present invention will be explained in more detail by Preparation Examples, Formulation Examples and Test Examples, but the present invention is not limited to these Examples.

First, Preparation Examples of the present compound and Reference Preparation Examples for preparing intermediates of the present compound will be described.

Preparation Example 1

110 mg of methyl 4-hydroxy-1-methyl-2-oxo-1,2-dihydropyridine-3-carboxylate and 83.9 mg of 2-aminobenzoimidzole were added to 15 ml of bromobenzene, then, the mixture was stirred for 4 hours under heat refluxing condition. The reaction mixture was cooled to room temperature, then, to the reaction mixture was added 30 ml of n-hexane. The resulting solid was collected by filtration, and washed with n-hexane and dried to obtain 115 mg of N-(2-benzimidazolyl)-4-hydroxy-1-methyl-2-oxo-1,2-dihydropyridine-3-carboxamide (hereinafter, referred to as present compound 1) represented by the formula:

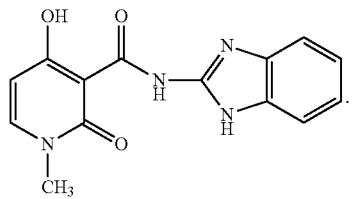

$^1$H-NMR(CD$_3$SOCD$_3$, TMS) δ(ppm): 3.52 (3H, s), 6.28 (1H, d, J=8 Hz), 7.12 (2H, m), 7.50 (2H, m), 8.04 (1H, d, J=8 Hz), 12.22 (1H, s), 13.31 (1H, s)

Preparation Example 2

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate and according to the same manner as that of Preparation Example 1, N-(2-benzimidazolyl)-1,6-dimethyl-4-hydroxy-2-oxo-1,2-dihydropyridine-3-carboxamide represented by the formula:

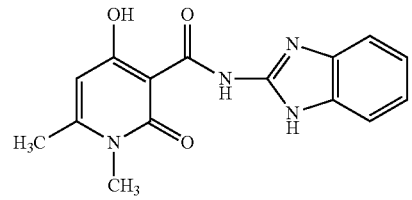

(hereinafter, referred to as present compound 2) was obtained.

$^1$H-NMR(CD$_3$SOCD$_3$, TMS) δ(ppm): 2.45 (3H, s), 3.50 (3H, s), 6.26 (1H, s), 7.13 (2H, m), 7.48 (2H, m), 12.19 (1H, s), 13.32 (1H, s), 14.28 (1H, s)

Preparation Example 3

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 5-amino-3-trifluoromethyl-1,2,4-thiadiazol in place of 2-aminobenzimidazole and according to the same manner as that of Preparation Example 1, N-(3-trifluoromethyl-1,2,4-thiadiazol-5-yl)-1,6-dimethyl-4-hydroxy-2-oxo-1,2-dihydropyridine-3-carboxamide represented by the formula:

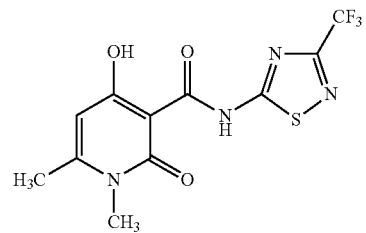

(hereinafter, referred to as present compound 3) was obtained.

$^1$H-NMR(CDCl$_3$, TMS) δ(ppm): 2.44 (3H, s), 3.58 (3H, s), 6.06 (1H, s), 13.34 (1H, s), 14.07 (1H, s)

Preparation Example 4

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 2-amino-5-fluorobenzimidazole in place of 2-aminobenzimidazole and according to the same manner as that of Preparation Example 1, N-(5-fluoro-2-benzimidazolyl)-1,6-dimethyl-4-hydroxy-2-oxo-1,2-dihydropyridine-3-carboxamide represented by the formula:

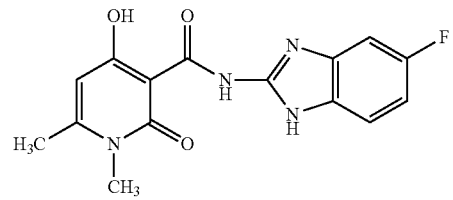

(hereinafter, referred to as present compound 4) was obtained.

$^1$H-NMR(CD$_3$SOCD$_3$, TMS) δ(ppm): 2.45 (3H, s), 3.49 (3H, s), 6.26 (1H, s), 6.97 (1H, m), 7.26 (1H, m), 7.47 (1H, m), 12.28 (1H, s), 13.37 (1H, s), 14.20 (1H, s)

Preparation Example 5

Using 2-amino-5-fluorobenzimidazole in place of 2-aminobenzimidazole and according to the same manner as that of Preparation Example 1, N-(5-fluoro-2-benzimidazolyl)-4-hydroxy-1-methyl-2-oxo-1,2-dihydropyridine-3-carboxamide represented by the formula:

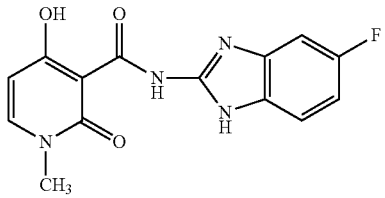

(hereinafter, referred to as present compound 5) was obtained.

$^1$H-NMR(CD$_3$SOCD$_3$, TMS) δ(ppm): 3.52 (3H, s), 6.27 (1H, d, J=7 Hz), 6.98 (1H, m), 7.26 (1H, d, J=7 Hz), 7.47 (1H, m), 8.04 (1H, d, J=8 Hz), 12.31 (1 H, s), 13.37 (1H, s), 14.32 (1H, s)

Preparation Example 6

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 2-amino-5-chlorobenzimidazole in place of 2-aminobenzimidazole and according to the same manner as that of Preparation Example 1, N-(5-chloro-2-benzimidazolyl)-1,6-dimethyl-4-hydroxy-2-oxo-1,2-dihydropyridine-3-carboxamide represented by the formula:

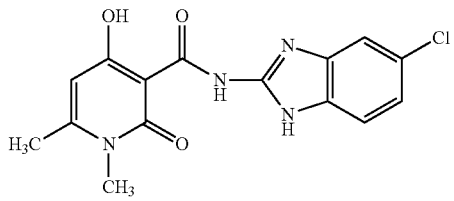

(hereinafter, referred to as present compound 6) was obtained.

$^1$H-NMR (CD$_3$SOCD$_3$, TMS) δ(ppm): 2.45 (3H, s), 3.49 (3H, s), 6.26 (1H, s), 7.14 (1H, m), 7.43-7.52 (2H, m), 12.33 (1H, s), 13.40 (1H, s), 14.16 (1 H, s)

Preparation Example 7

Using ethyl 1-ethoxymethyl-4-hydroxy-2-oxo-1,2-dihydropyridine-3-carboxylate in place of methyl 4-hydroxy-1-methyl-2-oxo-1,2-dihydropyridine-3-carboxylate and according to the same manner as that of Preparation Example 1, N-(5-fluoro-2-benzimidazolyl)-1-ethoxymethyl-4-hydroxy-2-oxo-1,2-dihydropyridine-3-carboxamide represented by the formula:

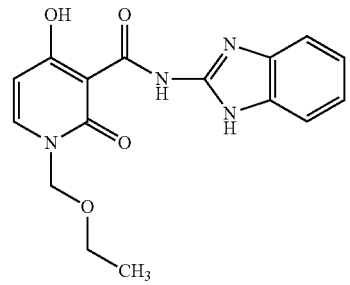

(hereinafter, referred to as present compound 7) was obtained.

$^1$H-NMR(CD$_3$SOCD$_3$, TMS) δ(ppm): 1.12 (3H, t, J=7 Hz), 3.58 (2H, q, J=7 Hz), 5.35 (2H, s), 6.31 (1H, d, J=8 Hz), 7.13 (2H, m), 7.47 (2H, m), 8.04 (1H, d, J=8 Hz), 12.20 (1H, m), 13.17 (1H, m)

Preparation Example 8

Using a carboxylate compound represented by the formula:

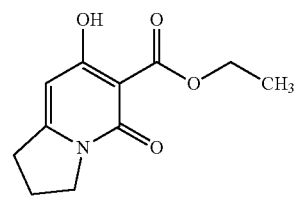

in place of methyl 4-hydroxy-1-methyl-2-oxo-1,2-dihydropyridine-3-carboxylate and according to the same manner as that of Preparation Example 1, a carboxamide compound represented by the formula:

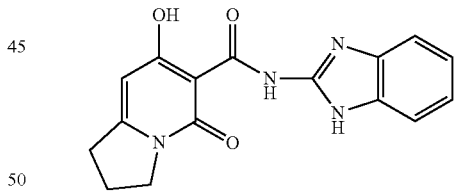

(hereinafter, referred to as present compound 8) was obtained.

$^1$H-NMR(CD$_3$SOCD$_3$, TMS) δ(ppm): 2.15 (2H, m) 3.14 (2H, t, J=8 Hz), 4.07 (2H, t, J=7 Hz), 6.26 (1H, s), 7.14 (2H, m), 7.48 (2H, m), 12.20 (1H, bs), 13.22 (1H, s)

Preparation Example 9

Using methyl 1-ethyl-4-hydroxy-2-oxo-1,2-dihydropyridine-3-carboxylate in place of methyl 4-hydroxy-1-methyl-2-oxo-1,2-dihydropyridine-3-carboxylate and according to the same manner as that of Preparation Example 1, N-(2-benzimidazolyl)-1-ethyl-4-hydroxy-2-oxo-1,2-dihydropyridine-3-carboxamide represented by the formula:

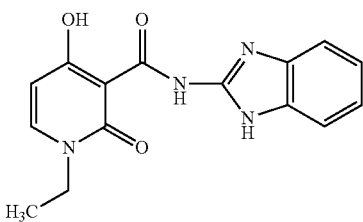

(hereinafter, referred to as present compound 9) was obtained.

$^1$H-NMR(CD$_3$SOCD$_3$, TMS) δ(ppm): 1.27 (3H, d, J=7 Hz), 4.00 (2H, q, J=7 Hz), 6.30 (1H, d, J=7 Hz), 7.14 (2H, m), 7.49 (2H, m), 8.07 (1H, d, J=7 Hz), 13.35 (1H, s)

Preparation Example 10

Using 2-amino-4,5-dicyanoimidazole in place of 2-aminobenzimidazole and according to the same manner as that of Preparation Example 1, N-(4,5-dicyano-2-imidazolyl)-4-hydroxy-1-methyl-2-oxo-1,2-dihydropyridine-3-carboxamide represented by the formula:

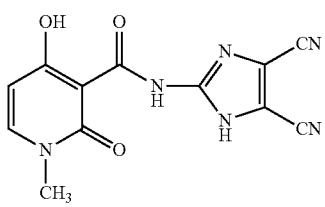

(hereinafter, referred to as present compound 10) was obtained.

Preparation Example 11

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 3-aminopyrazole in place of 2-aminobenzimidazole and according to the same manner as that of Preparation Example 1, N-(3-pyrazolyl)-1,6-dimethyl-4-hydroxy-2-oxo-1,2-dihydropyridine-3-carboxamide represented by the formula:

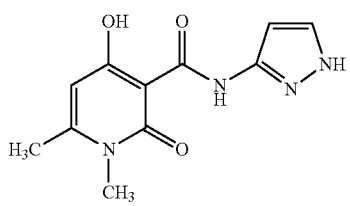

(hereinafter, referred to as present compound 11) was obtained.

$^1$H-NMR(CD$_3$SOCD$_3$, TMS) δ(ppm): 2.51 (3H, s), 3.52 (3H, s), 6.16 (1H, s), 6.59 (1H, s), 7.69 (1H, s), 12.58 (1H, s), 12.63 (1H, s)

Preparation Example 12

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 2-amino-5-methyl-1,3,4-thiadiazole in place of 2-aminobenzimidazole and according to the same manner as that of Preparation Example 1, N-(5-methyl-1,3,4-thiadiazol-2-yl)-1,6-dimethyl-4-hydroxy-2-oxo-1,2-dihydropyridine-3-carboxamide (hereinafter, referred to as present compound 12) represented by the formula:

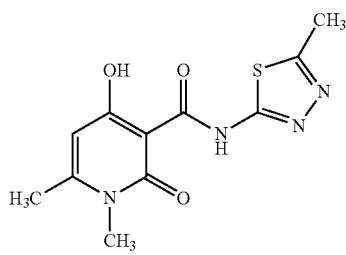

was obtained.

$^1$H-NMR(CDCl$_3$, TMS) δ(ppm): 2.41 (3H, s), 2.72 (3H, s), 3.54 (3H, s), 6.01 (1H, s), 13.66 (1H, s), 13.80 (1H, s)

Preparation Example 13

Using ethyl 1,6-dimethyl-4-hydroxy-2-oxo-1,2-dihydropyridine-3-carboxylate in place of methyl 4-hydroxy-1-methyl-2-oxo-1,2-dihydropyridine-3-carboxylate, using 2-aminothiazole in place of 2-aminobenzimidazole and according to the same manner as that of Preparation Example 1, N-(2-thiazolyl)-1,6-dimethyl-4-hydroxy-2-oxo-1,2-dihydropyridine-3-carboxamide represented by the formula:

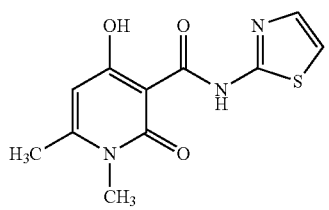

(hereinafter, referred to as present compound 13) was obtained.

$^1$H-NMR(CDCl$_3$, TMS) δ(ppm): 2.39 (3H, s), 3.53 (3H, s), 5.99 (1H, s), 7.02 (1H, d, J=3 Hz), 7.52 (1H, d, J=3 Hz), 13.49 (1H, s), 14.09 (1H, s)

Preparation Example 14

197 mg of ethyl 5-chloro-1,6-dimethyl-4-hydroxy-2-oxo-1,2-dihydropyridine-3-carboxylate and 76 mg of 2-amino-1,3,4-thiadiazole were added to 2 ml of bromobenzene, then, the mixture was stirred for 5 hours under heat refluxing condition. The reaction mixture was cooled to room temperature, then, to the reaction mixture was added n-hexane. The resulting solid was collected by filtration, and washed with a mixture of t-butyl methyl ether and n-hexane and dried to obtain 183 mg of N-(1,3,4-thiadiazol-2-yl)-5-chloro-1,6-dimethyl-4-hydroxy-2-oxo-1,2-dihydropyridine-3-carboxamide (hereinafter, referred to as present compound 14) represented by the formula:

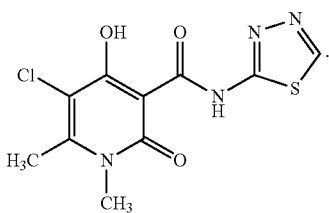

$^1$H-NMR(CDCl$_3$, TMS) δ(ppm): 2.64 (3H, s), 3.65 (3H, s), 8.90 (1H, s), 13.85 (1H, s), 14.63 (1H, s)

Preparation Example 15

Using ethyl 5-fluoro-1,6-dimethyl-4-hydroxy-2-oxo-1,2-dihydropyridine-3-carboxylate in place of ethyl 5-chloro-1,6-dimethyl-4-hydroxy-2-oxo-1,2-dihydropyridine-3-carboxylate, using 2-amino-5-methylthiazole in place of 2-amino-1,3,4-thiadiazole and according to the same manner as that of Preparation Example 12, N-(5-methyl-2-thiazolyl)-5-fluoro-1,6-dimethyl-4-hydroxy-2-oxo-1,2-dihydropyridine-3-carboxamide represented by the formula:

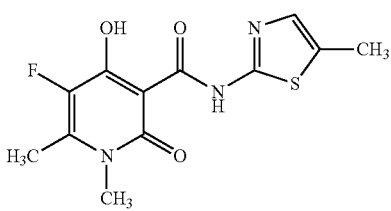

(hereinafter, referred to as present compound 15) was obtained.
$^1$H-NMR(CDCl$_3$, TMS) δ(ppm): 2.42 (3H, s), 2.43 (3H, d, J=3 Hz), 3.54 (3H, s), 7.17 (1H, d, J=1 Hz), 13.32 (1H, s), 14.69 (1H, s)

Preparation Example 16

213 mg of ethyl 1,6-dimethyl-4-hydroxy-2-oxo-1,2-dihydropyridine-3-carboxylate and 94 mg of 2-amino-1,3,4-thiadiazole were added to 2.5 ml of bromobenzene, then, the mixture was stirred for 6.5 hours under heat refluxing condition. The reaction mixture was cooled to room temperature, then, the resulting solid was collected by filtration, and washed with a mixed solvent of t-butyl methyl ether and hexane and dried to obtain 185 mg of 1,6-dimethyl-4-hydroxy-2-oxo-N-(1,3,4-thiadiazol-2-yl)-1,2-dihydropyridine-3-carboxamide (hereinafter, referred to as present compound 16) represented by the formula:

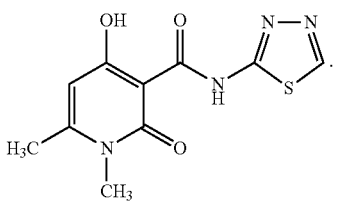

$^1$H-NMR(CDCl$_3$, TMS) δ(ppm): 2.41 (3H, s), 3.54 (3H, s), 6.01 (1H, s), 8.88 (1H, s), 13.67 (1H, s), 13.84 (1H, s)

Preparation Example 17

212 mg of ethyl 1,6-dimethyl-4-hydroxy-2-oxo-1,2-dihydropyridine-3-carboxylate and 117 mg of 2-amino-5-ethyl-1,3,4-thiadiazole were added to 2.5 ml of bromobenzene, then, the mixture was stirred for 5 hours under heat refluxing condition. The reaction mixture was cooled to room temperature. The resulting solid was collected by filtration, and washed with a mixed solvent of t-butyl methyl ether and hexane and dried to obtain 200 mg of N-(5-ethyl-1,3,4-thiadiazol-2-yl)-1,6-dimethyl-4-hydroxy-2-oxo-1,2-dihydropyridine-3-carboxamide (hereinafter, referred to as present compound 17) represented by the formula:

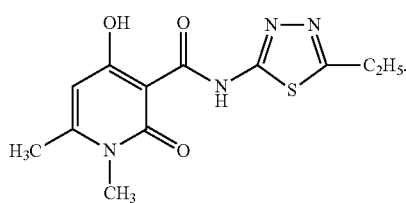

$^1$H-NMR(CDCl$_3$, TMS) δ(ppm): 1.43 (3H, t, J=8 Hz), 2.41 (3H, s), 3.08 (2H, q, J=8 Hz), 3.53 (3H, s), 6.00 (1H, s), 13.65 (1H, s), 13.81 (1H, s)

Preparation Example 18

243 mg of ethyl 1,6-dimethyl-4-hydroxy-2-oxo-1,2-dihydropyridine-3-carboxylate and 122 mg of 2-amino-3-methyl-1,2,4-thiadiazole were added to 2.5 ml of bromobenzene, then, the mixture was stirred for 5 hours under heat refluxing condition. The reaction mixture was cooled to room temperature. The resulting solid was collected by filtration, and washed with a mixed solvent of t-butyl methyl ether and hexane and dried to obtain 257 mg of 1,6-dimethyl-4-hydroxy-N-(3-methyl-1,2,4-thiadiazol-5-yl)-2-oxo-1,2-dihydropyridine-3-carboxamide (hereinafter, referred to as present compound 18) represented by the formula:

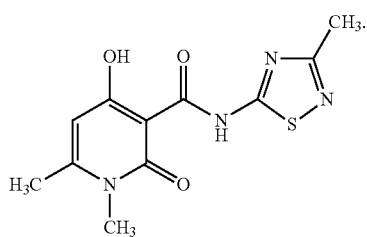

$^1$H-NMR(CDCl$_3$, TMS) δ(ppm): 2.42 (3H, s), 2.58 (3H, s), 3.54 (3H, s), 6.04 (1H, s), 13.53 (1H, s), 13.61 (1H, s)

Preparation Example 19

213 mg of ethyl 1,6-dimethyl-4-hydroxy-2-oxo-1,2-dihydropyridine-3-carboxylate and 120 mg of 5-amino-3-ethyl-1,2,4-thiadiazole were added to 2.5 ml of bromobenzene, then, the mixture was stirred for 4 hours under heat refluxing condition. The reaction mixture was cooled to room temperature. The resulting solid was collected by filtration, and washed with a mixed solvent of t-butyl methyl ether and hexane and dried to obtain 231 mg of 1,6-dimethyl-N-(3-ethyl-1,2,4-thiadiazol-5-yl)-4-hydroxy-2-oxo-1,2-dihydropyridine-3- carboxamide (hereinafter, referred to as present compound 19) represented by the formula:

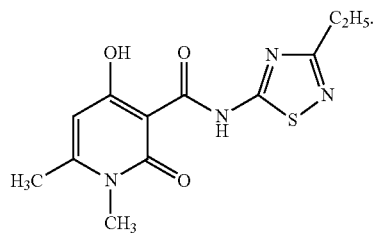

¹H-NMR(CDCl₃, TMS) δ(ppm): 1.37 (3H, t, J=7 Hz), 2.42 (3H, s), 2.91 (2H, q, J=7 Hz), 3.54 (3H, s), 6.03 (1H, s), 13.55 (1H, s), 13.59 (1H, s)

Preparation Example 20

212 mg of ethyl 1,6-dimethyl-4-hydroxy-2-oxo-1,2-dihydropyridine-3-carboxylate and 105 mg of 2-amino-5-methylthiazole were added to 2.5 ml of bromobenzene, then, the mixture was stirred for 5.5 hours under heat refluxing condition. The reaction mixture was cooled to room temperature. The resulting solid was collected by filtration, and washed with a mixed solvent of t-butyl methyl ether and hexane and dried to obtain 188 mg of 1,6-dimethyl-4-hydroxy-N-(5-methylthiazol-2-yl)-2-oxo-1,2-dihydropyridine-3-carboxamide (hereinafter, referred to as present compound 20) represented by the formula:

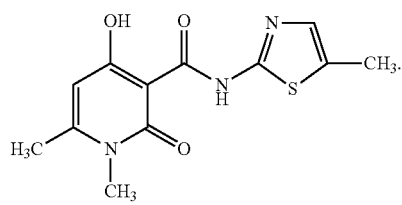

¹H-NMR(CDCl₃, TMS) δ(ppm): 2.39 (3H, s), 2.42 (3H, s), 3.52 (3H, s), 5.99 (1H, s), 7.16 (1H, s), 13.33 (1H, s), 14.17 (1H, s)

Preparation Example 21

210 mg of ethyl 1,6-dimethyl-4-hydroxy-2-oxo-1,2-dihydropyridine-3-carboxylate and 117 mg of 2-amino-4-ethylthiazole were added to 2.5 ml of bromobenzene, then, the mixture was stirred for 5.5 hours under heat refluxing condition. The reaction mixture was cooled to room temperature. The resulting solid was collected by filtration, and washed with a mixed solvent of t-butyl methyl ether and hexane and dried to obtain 150 mg of 1,6-dimethyl-N-(4-ethylthiazol-2-yl)-4-hydroxy-2-oxo-1,2-dihydropyridine-3-carboxamide (hereinafter, referred to as present compound 21) represented by the formula:

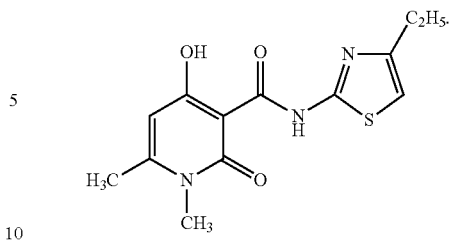

¹H-NMR(CDCl₃, TMS) δ(ppm): 1.28 (3H, t, J=7 Hz), 2.39 (3H, s), 2.72 (2H, q, J=7 Hz), 3.52 (3H, s), 5.99 (1H, s), 6.57 (1H, s), 13.41 (1H, s), 14.14 (1H, s)

Preparation Example 22

223 mg of ethyl 1,6-dimethyl-4-hydroxy-2-oxo-1,2-dihydropyridine-3-carboxylate and 129 mg of 2-amino-5-chlorothiazole were added to 2.5 ml of bromobenzene, then, the mixture was stirred for 8.5 hours under heat refluxing condition. The reaction mixture was cooled to room temperature. The resulting solid was collected by filtration, and washed with a mixed solvent of t-butyl methyl ether and hexane and dried to obtain 153 mg of N-(5-chlorothiazol-2-yl)-1,3-dimethyl-4-hydroxy-2-oxo-1,2-dihydropyridine-3-carboxamide (hereinafter, referred to as present compound 22) represented by the formula:

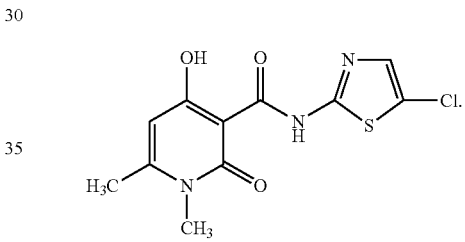

¹H-NMR(CDCl₃, TMS) δ(ppm): 2.41 (3H, s), 3.53 (3H, s), 6.01 (1H, s), 7.33 (1H, s), 13.44 (1H, s), 13.84 (1H, s)

Preparation Example 23

213 mg of ethyl 1,6-dimethyl-4-hydroxy-2-oxo-1,2-dihydropyridine-3-carboxylate and 78 mg of 3-amino-1,2,4-triazole were added to 2.5 ml of bromobenzene, then, the mixture was stirred for 7.5 hours under heat refluxing condition. The reaction mixture was cooled to room temperature. The resulting solid was collected by filtration, and washed with a mixed solvent of t-butyl methyl ether and hexane and dried to obtain 188 mg of 1,6-dimethyl-4-hydroxy-2-oxo-N-(1,2,4-triazol-3-yl)-1,2-dihydropyridine-3-carboxamide (hereinafter, referred to as present compound 23) represented by the formula:

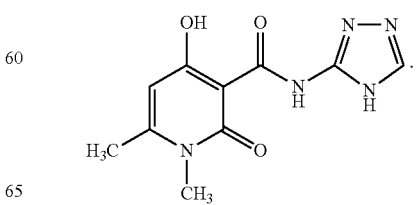

$^1$H-NMR(CDCl$_3$, TMS) δ(ppm): 2.42 (3H, s), 3.53 (3H, s), 6.02 (1H, s), 7.79 (1H, s), 13.29 (1H, s), 13.86 (1H, s)

Preparation Example 24

211 mg of ethyl 1,6-dimethyl-4-hydroxy-2-oxo-1,2-dihydropyridine-3-carboxylate and 90 mg of 3-amino-5-methyl-1,2,4-triazole were added to 2.5 ml of bromobenzene, then, the mixture was stirred for 7 hours under heat refluxing condition. The reaction mixture was cooled to room temperature. The resulting solid was collected by filtration, and washed with a mixed solvent of t-butyl methyl ether and hexane and dried to obtain 214 mg of 1,6-dimethyl-4-hydroxy-N-(5-methyl-1,2,4-triazol-3-yl)-2-oxo-1,2-dihydropyridine-3-carboxamide (hereinafter, referred to as present compound 24) represented by the formula:

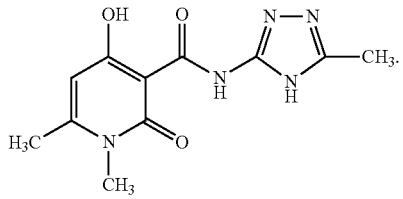

$^1$H-NMR(CDCl$_3$, TMS) δ(ppm): 2.38 (3H, s), 2.40 (3H, s), 3.52 (3H, s), 6.00 (1H, s), 7.79 (1H, s), 13.19 (1H, s), 13.94 (1H, s)

Preparation Example 25

213 mg of ethyl 1,6-dimethyl-4-hydroxy-2-oxo-1,2-dihydropyridine-3-carboxylate and 79 mg of 3-amino-1-methylpyrazole were added to 2.5 ml of bromobenzene, then, the mixture was stirred for 6.5 hours under heat refluxing condition. The reaction mixture was cooled to room temperature. The resulting solid was collected by filtration, and washed with a mixed solvent of t-butyl methyl ether and hexane and dried to obtain 134 mg of 1,6-dimethyl-4-hydroxy-N-(1-methylpyrazol-3-yl)-2-oxo-1,2-dihydropyridine-3-carboxamide (hereinafter, referred to as present compound 25) represented by the formula:

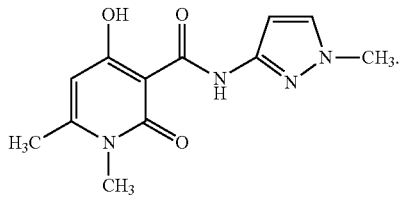

$^1$H-NMR(CDCl$_3$, TMS) δ(ppm): 2.37 (3H, s), 3.50 (3H, s), 3.84 (3H, s), 5.95 (1H, s), 6.59 (1H, s), 6.61 (1H, d, J=2 Hz), 12.48 (1H, s), 15.25 (1H, s)

Preparation Example 26

257 mg of ethyl 1,6-dimethyl-4-hydroxy-2-oxo-1,2-dihydropyridine-3-carboxylate and 260 mg of 2-aminoimidazole were added to 5 ml of bromobenzene, then, the mixture was stirred for 2 hours under heat refluxing condition. Further, to the mixture was added 151 mg of ethyl 1,6-dimethyl-4-hydroxy-2-oxo-1,2-dihydropyridine-3-carboxylate, and the resultant mixture was stirred for 2.5 hours under heat refluxing condition. The reaction mixture was cooled to room temperature. The resulting solid was collected by filtration, and washed with a mixed solvent of t-butyl methyl ether and hexane and dried to obtain 580 mg of 1,6-dimethyl-4-hydroxy-N-(2-imidazolyl)-2-oxo-1,2-dihydropyridine-3-carboxamide (hereinafter, referred to as present compound 26) represented by the formula:

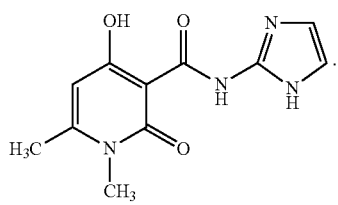

$^1$H-NMR(CDCl$_3$, TMS) δ(ppm): 2.39 (3H, s), 3.52 (3H, s), 5.98 (1H, s), 6.85 (1H, d, J=1 Hz), 6.90 (1H, d, J=1 Hz), 10.60 (1H, s), 13.06 (1H, s), 14.29 (1H, s)

Preparation Example 27

213 mg of ethyl 1,6-dimethyl-4-hydroxy-2-oxo-1,2-dihydropyridine-3-carboxylate and 79 mg of 3-amino-5-methylisooxazole were added to 2.5 ml of bromobenzene, then, the mixture was stirred for 6.5 hours under heat refluxing condition. The reaction mixture was cooled to room temperature. The resulting solid was collected by filtration, and washed with a mixed solvent of t-butyl methyl ether and hexane and dried to obtain 141 mg of 1,6-dimethyl-4-hydroxy-N-(5-methylisooxazol-3-yl)-2-oxo-1,2-dihydropyridine-3-carboxamide (hereinafter, referred to as present compound 27) represented by the formula:

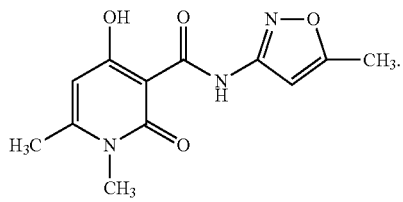

$^1$H-NMR(CD$_3$SOCD$_3$, TMS) δ(ppm): 2.42 (3H, s), 2.42 (3H, s), 3.51 (3H, s), 5.98 (1H, s), 6.66 (1H, s), 12.72 (1H, s), 14.65 (1H, s)

Preparation Example 28

199 mg of ethyl 5-chloro-1,6-dimethyl-4-hydroxy-2-oxo-1,2-dihydropyridine-3-carboxylate and 98 mg of 2-aminobenzimidazole were added to 2 ml of bromobenzene, then, the mixture was stirred for 9.5 hours under heat refluxing condition. The reaction mixture was cooled to room temperature, then, hexane was added to this and the resultant mixture was allowed to stand still. The resulting solid was collected by filtration, and washed with a mixture of t-butyl methyl ether and n-hexane and dried to obtain 202 mg of N-(2-benzimidazolyl)-5-chloro-1,6-dimethyl-4-hydroxy-2-oxo-1,2-dihydropyridine-3-carboxamide (hereinafter, referred to as present compound 28) represented by the formula:

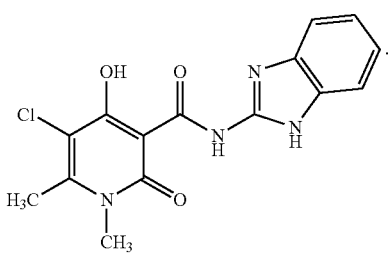

¹H-NMR(CDCl₃, TMS) δ(ppm): 2.62 (3H, s), 3.63 (3H, s), 7.18-7.72 (5H, m), 10.76 (1H, s), 13.41 (1H, s)

Preparation Example 29

161 mg of ethyl 5-chloro-1,6-dimethyl-4-hydroxy-2-oxo-1,2-dihydropyridine-3-carboxylate and 51 mg of 3-amino-1,2,4-triazole were added to 1.5 ml of bromobenzene, then, the mixture was stirred for 5 hours under heat refluxing condition. The reaction mixture was cooled to room temperature, then, hexane was added to this and the resultant mixture was allowed to stand still. The resulting solid was collected by filtration, and washed with a mixture of t-butyl methyl ether and n-hexane and dried to obtain 153 mg of 5-chloro-1,6-dimethyl-4-hydroxy-2-oxo-N-(1,2,4-triazol-3-yl)-1,2-dihydropyridine-3-carboxamide (hereinafter, referred to as present compound 29) represented by the formula:

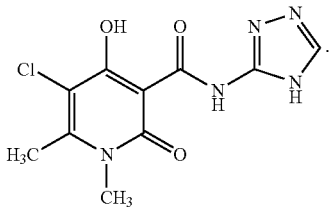

¹H-NMR(CDCl₃, TMS) δ(ppm): 2.64 (3H, s), 3.63 (3H, s), 7.81 (1H, s), 13.30 (1H, s), 14.80 (1H, s)

Preparation Example 30

160 mg of ethyl 5-chloro-1,6-dimethyl-4-hydroxy-2-oxo-1,2-dihydropyridine-3-carboxylate and 60 mg of 2-aminothiazole were added to 1.5 ml of bromobenzene, then, the mixture was stirred for 5 hours under heat refluxing condition. The reaction mixture was cooled to room temperature, then, hexane was added to this and the resultant mixture was allowed to stand still. The resulting solid was collected by filtration, and washed with a mixture of t-butyl methyl ether and n-hexane and dried to obtain 136 mg of 5-chloro-1,6-dimethyl-4-hydroxy-2-oxo-N-(2-thiazolyl)-1,2-dihydropyridine-3-carboxamide (hereinafter, referred to as present compound 30) represented by the formula:

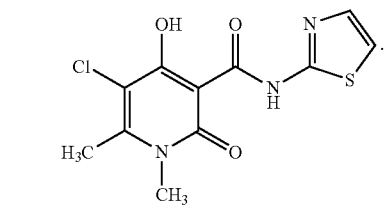

¹H-NMR(CDCl₃, TMS) δ(ppm): 2.62 (3H, s), 3.62 (3H, s), 7.05 (1H, d, J=3 z), 7.54 (1H, d, J=3 Hz), 13.48 (1H, s), 15.07 (1H, s)

Preparation Example 31

200 mg of 5-fluoro-1,6-dimethyl-4-hydroxy-2-oxo-1,2-dihydropyridine-3-carboxylic acid was dissolved in 3 ml of acetonitrile, and 162 mg of carbonyldiimidazole was added to this. The mixture was stirred for 1 hour under heat refluxing condition, then, 114 mg of 2-amino-4-methylthiazole was added, and the resulting mixture was further stirred for 1 hour under heat refluxing condition. Thereafter, the reaction mixture was cooled to room temperature. As a result, a crystal was produced. The produced crystal was collected by filtration, to obtain 90 mg of 5-fluoro-1,6-dimethyl-4-hydroxy-2-oxo-N-(4-methyl-2-thiazolyl)-1,2-dihydropyridine-3-carboxamide (hereinafter, referred to as present compound 31) represented by the formula:

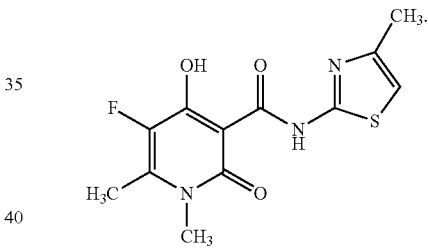

¹H-NMR(CDCl₃, TMS) δ(ppm): 2.29 (3H, s), 2.43 (3H, s), 3.50 (3H, s), 6.97 (1H, s), 13.75 (1H, s), 14.37 (1H, s)

Then, Reference Preparation Examples for preparing intermediates of the present compound will be described.

Reference Preparation Example 1

At room temperature, 7.9 ml of trimethylsilylazide was added to a mixture of 5.0 g of maleic anhydride and 20 ml of benzene. The mixture was stirred at 50-60° C. for 3 hours. After cooling the reaction mixture to room temperature, 4.5 ml of ethanol was added, followed by stirring for additional 3 hours. The resulting solid was collected by filtration, and washed with diethyl ether to obtain 300 mg of 2H-1,3-oxazine-2,6(3H)-dione represented by the formula:

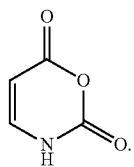

$^1$H-NMR (CD$_3$SOCD$_3$, TMS) δ (ppm): 5.62 (1H, d, J=8 Hz), 7.66 (1H, d, J=8 Hz), 11.55 (1H, s)

Reference Preparation Example 2

At room temperature, 50.0 g of trimethylsilylazide was added to a mixture of 44.8 g of citraconic anhydride and 60 ml of chloroform. The mixture was stirred at 50-60° C. for 5 hours. After cooling the reaction mixture with an ice, 25.0 g of ethanol was added, followed by stirring for additional 30 minutes. The resulting solid was collected by filtration, and washed with a mixed solvent of chloroform and ethanol to obtain crude 4-methyl-2H-1,3-oxazine-2,6(3H)-dione represented by the formula:

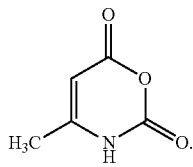

Further, the washing solution was concentrated under reduced pressure. T-butyl methyl ether was added to the residue, followed by filtration. The resulting solid was washed with t-butyl methyl ether. The filtrate and the washing solution were combined and concentrated under reduced pressure to obtain crude 5-methyl-2H-1,3-oxazine-2,6(3H)-dione represented by the formula:

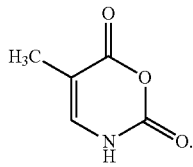

4-Methyl-2H-1,3-oxazine-2,6(3H)-dione $^1$H-NMR(CD$_3$SOCD$_3$, TMS) δ(ppm): 2.06 (3H, s), 5.50 (1H, s), 11.47 (1H, s-br)

5-Methyl-2H-1,3-oxazine-2,6(3H)-dione $^1$H-NMR(CD$_3$SOCD$_3$, TMS) δ(ppm): 1.78 (3H, s), 7.48 (1H, s), 11.47 (1H, s-br)

Reference Preparation Example 3

At room temperature, 1.50 g of 2H-1,3-oxazine-2,6(3H)-dione, 2.19 g of potassium carbonate and 3.77 g of methyl iodide were sequentially added to 30 ml of acetone, and the mixture was stirred for 10 hours under heat refluxing condition. The reaction mixture was cooled to room temperature and filtered. The filtrate was concentrated under reduced pressure, and the resulting solid was dried to obtain 1.46 g of 3-methyl-2H-1,3-oxazine-2,6(3H)-dione represented by the formula:

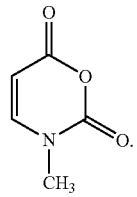

$^1$HNMR(CD$_3$SOCD$_3$, TMS) δ(ppm): 3.26 (3H, s), 5.68 (1H, d, J=8 Hz), 7.82 (1H, d, J=8 Hz)

Reference Preparation Example 4

Using crude 4-methyl-2H-1,3-oxazine-2,6(3H)-dione in place of 2H-1,3-oxazine-2,6(3H)-dione and according to the same manner as that of Reference Preparation Example 3, crude 3,4-dimethyl-2H-1,3-oxazine-2,6(3H)-dione represented by the formula:

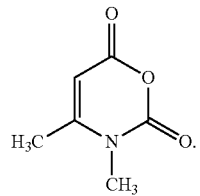

was obtained.

$^1$H-NMR(CDCl$_3$, TMS) δ(ppm): 2.27 (3H, d), 3.41 (3H, s), 5.49 (1H, d)

Reference Preparation Example 5

Using ethyl bromide in place of methyl iodide and according to the same manner as that of Reference Preparation Example 3, 3-ethyl-2H-1,3-oxazine-2,6(3H)-dione represented by the formula:

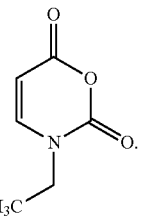

was obtained.

Reference Preparation Example 6

Using chloromethyl ethyl ether in place of methyl iodide and according to the same manner as that of Reference Preparation Example 3, 3-ethoxymethyl-2H-1,3-oxazine-2,6(3H)-dione represented by the formula:

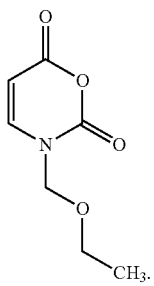

was obtained.

Reference Preparation Example 7

Using crude 5-methyl-2H-1,3-oxazine-2,6(3H)-dione in place of 2H-1,3-oxazine-2,6(3H)-dione and according to the same manner as that of Reference Preparation Example 3, crude 3,5-dimethyl-2H-1,3-oxazine-2,6(3H)-dione represented by the formula:

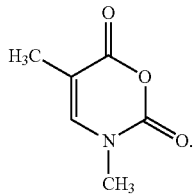

was obtained.

$^1$H-NMR (CDCl$_3$, TMS) δ (ppm): 1.94 (3H, d), 3.37 (3H, s), 6.99 (1H, q-like)

Reference Preparation Example 8

Using 4,5-dimethyl-2H-1,3-oxazine-2,6(3H)-dione represented by the formula:

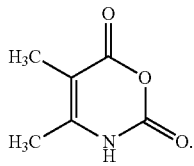

in place of 2H-1,3-oxazine-2,6(3H)-dione and according to the same manner as that of Reference Preparation Example 3, 3,4,5-trimethyl-2H-1,3-oxazine-2,6(3H)-dione represented by the formula:

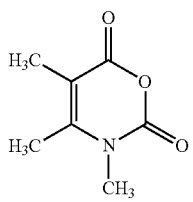

was obtained.

$^1$H-NMR(CDCl$_3$, TMS) δ(ppm): 1.97 (3H, s), 2.26 (3H, s), 3.42 (3H, s)

Reference Preparation Example 9

Under ice cooling, 568 mg of sodium hydride (60%) was added to a mixture of 181 mg of dimethyl malonate and 70 ml of N,N-dimethylformamide and the mixture was stirred for 20 minutes. After the mixture was heated to 80° C., 1.50 g of 3-methyl-2H-1,3-oxazine-2,6(3H)-dione was added to the mixture, followed by further stirring at 120° C. for 7 hours. The reaction mixture was concentrated under reduced pressure, 2 mol/L hydrochloric acid was added to the residue, and the mixture was stirred at 60° C. for 15 minutes. The mixture was extracted with ethyl acetate. The organic layer was washed with an aqueous saturated sodium chloride solution, dried with sodium sulfate, filtered, and concentrated. The residue was subjected to silica gel column chromatography (eluent: ethyl acetate) to obtain 100 mg of methyl 4-hydroxy-1-methyl-2-oxo-1,2-dihydropyridine-3-carboxylate represented by the formula:

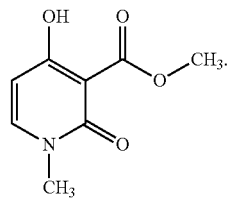

$^1$H-NMR (CDCl$_3$, TMS) δ (ppm): 3.44 (3H, s), 3.97 (3H, s), 5.97 (1H, d, J=8 Hz), 7.37 (1H, d, J=8 Hz), 13.21 (1H, s)

Reference Preparation Example 10

At room temperature, 1 ml of a solution of 0.71 g diethyl malonate in tetrahydrofuran was added to a mixture of 0.19 g of sodium hydride and 4 ml of tetrahydrofuran and the mixture was stirred for 20 minutes. At room temperature, 3 ml of a solution of 0.59 g 3,4-dimethyl-2H-1,3-oxazine-2,6(3H)-dione in tetrahydrofuran was added to the mixture, followed by stirring for 2 hours under heat refluxing condition. The reaction mixture was concentrated under reduced pressure. To the residue, 10 ml of water and 12 ml of 2 mol/L hydrochloric acid were added, followed by extraction with ethyl acetate. The organic layer was dried with magnesium sulfate, then filtered and concentrated to obtain 0.57 g of ethyl 1,6-dimethyl-4-hydroxy-2-oxo-1,2-dihydropyridine-3-carboxylate represented by the formula:

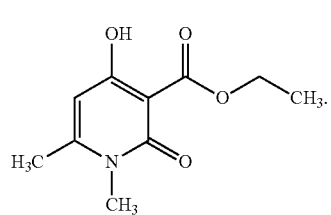

$^1$H-NMR(CDCl$_3$, TMS) δ(ppm): 1.44 (3H, t, J=7 Hz), 2.34 (3H, s), 3.45 (3H, s), 4.43 (2H, q, J=7 Hz), 5.86 (1H, s), 13.26 (1H, s)

Reference Preparation Example 11

Using 3-ethyl-2H-1,3-oxazine-2,6(3H)-dione in place of 3,4-dimethyl-2H-1,3-oxazine-2,6(3H)-dione and using dimethyl malonate in place of diethyl malonate and according to the same manner as that of Reference Preparation Example 10, methyl 1-ethyl-4-hydroxy-2-oxo-1,2-dihydropyridine-3-carboxylate represented by the formula:

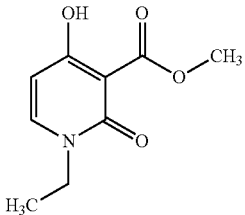

was obtained.

$^1$H-NMR (CDCl$_3$, TMS) δ (ppm): 1.33 (3H, t, J=7 Hz), 3.94 (2H, q, J=7 Hz), 3.98 (3H, s), 5.98 (1H, d, J=8 Hz), 7.37 (1H, d, J=8 Hz), 13.25 (1H, s)

Reference Preparation Example 12

Using 3-ethoxymethyl-2H-1,3-oxazine-2,6(3H)-dione in place of 3,4-dimethyl-2H-1,3-oxazine-2,6(3H)-dione and according to the same manner as that of Reference Preparation Example 10, ethyl 1-ethoxymethyl-4-hydroxy-2-oxo-1,2-dihydropyridine-3-carboxylate represented by the formula:

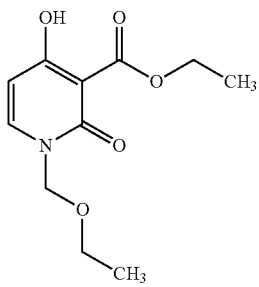

was obtained.

$^1$H-NMR (CDCl$_3$, TMS) δ (ppm): 1.20 (3H, t, J=7 Hz), 1.44 (3H, t, J=7 Hz), 3.60 (2H, q, J=7 Hz), 4.45 (2H, q, J=7 Hz), 5.30 (2H, s), 6.03 (1H, d, J=8 Hz), 7.50 (1H, d, J=8 Hz), 13.55 (1H, s)

Reference Preparation Example 13

Using 3,5-dimethyl-2H-1,3-oxazine-2,6(3H)-dione in place of 3,4-dimethyl-2H-1,3-oxazine-2,6(3H)-dione and according to the same manner as that of Reference Preparation Example 10, ethyl 1,5-dimethyl-4-hydroxy-2-oxo-1,2-dihydropyridine-3-carboxylate represented by the formula:

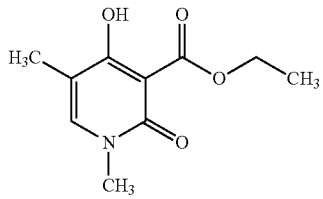

was obtained.

Reference Preparation Example 14

Using 3,4,5-trimethyl-2H-1,3-oxazine-2,6(3H)-dione in place of 3,4-dimethyl-2H-1,3-oxazine-2,6(3H)-dione, using dimethyl malonate in place of diethyl malonate and according to the same manner as that of Reference Preparation Example 10, methyl 4-hydroxy-2-oxo-1,5,6-trimethyl-1,2-dihydropyridine-3-carboxylate represented by the formula:

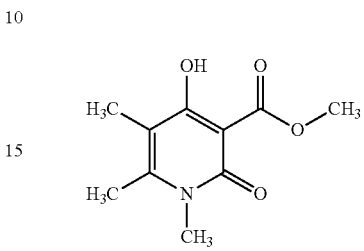

was obtained.

$^1$H-NMR(CDCl$_3$, TMS) δ(ppm): 2.05 (3H, s), 2.36 (3H, s), 3.51 (3H, s), 3.96 (3H, s), 13.83 (1H, s)

Reference Preparation Example 15

A mixture of 10.1 ml 2-methyl-1-pyrroline and 2.27 ml triethyl methanetricarboxylate was stirred at 200° C. for 20 hours. The reaction mixture was cooled to room temperature and subjected to silica gel column chromatography to obtain 400 mg of carboxylic ester represented by the formula:

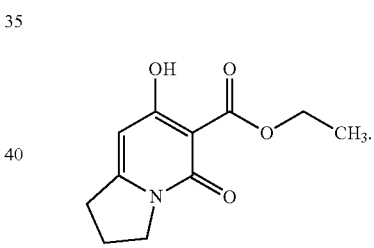

$^1$H-NMR(CDCl$_3$, TMS) δ(ppm): 1.43 (3H, t, J=7 Hz), 2.14 (2H, m), 3.06 (2H, t, J=7 Hz), 4.08 (2H, t, J=7 Hz), 4.41 (2H, q, J=7 Hz), 5.90 (1H, s), 13.35 (1H, s)

Reference Preparation Example 16

After 16.5 g of ethyl 2-chloroacetoacetate and 8.91 g of ethyl carbamate were sequentially added to 83.9 g of phosphorus oxychloride, this was stirred at 90° C. for 5 hours. The reaction mixture was concentrated under reduced pressure, and toluene and water were added to the residue, followed by separation of the layers. The organic layer was extracted with water four times. The aqueous layer was collected and extracted with ethyl acetate four times. The organic layer was collected, washed with water, dried with magnesium sulfate, filtered and concentrated. The resulting solid was washed with a mixture of t-butyl methyl ether and n-hexane and dried to obtain 5-chloro-4-methyl-2H-1,3-oxazine-2,6(3H)-dione represented by the formula:

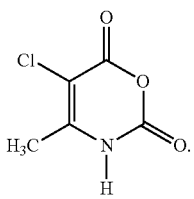

¹H-NMR (CDCl₃, TMS) δ(ppm): 2.34 (3H, s)

Reference Preparation Example 17

At room temperature, 2.11 g of 5-chloro-4-methyl-2H-1,3-oxazine-2,6(3H)-dione, 2.07 g of potassium carbonate and 1.3 ml of methyl iodide were sequentially added to 40 ml of acetone, then the mixture was stirred for 3 hours under heat refluxing condition. To the reaction mixture was added 0.5 ml of methyl iodide, and the mixture was further stirred for 2 hours under heat refluxing condition. The reaction mixture was cooled to room temperature and filtered. The filtrate was concentrated under reduced pressure. The resulting solid was dried to obtain 1.74 g of 5-chloro-3,4-dimethyl-2H-1,3-oxazine-2,6(3H)-dione represented by the formula:

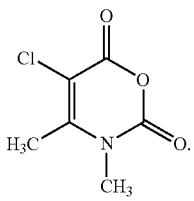

¹H-NMR(CDCl₃, TMS) δ(ppm): 2.48 (3H, s), 3.48 (3H, s)

Reference Preparation Example 18

To 0.43 g of sodium hydride (60%) was added 35 ml of tetrahydrofuran, 2.5 ml of a solution of 1.76 g diethyl malonate in tetrahydrofuran was further added under ice cooling, and the mixture was stirred at room temperature for 1 hour. To the mixture was added 1.74 g of 5-chrolo-3,4-dimethyl-2H-1,3-oxazine-2,6(3H)-dione, and this was stirred for 3.5 hours under heat refluxing condition. The reaction mixture was concentrated under reduced pressure. To the residue, 20 ml of water and 15 ml of 1 mol/L hydrochloric acid were sequentially added, followed by extraction with 85 ml of chloroform twice. The organic layer was dried with magnesium sulfate, filtered, and concentrated. The residue was washed with n-hexane to obtain 1.52 g of ethyl 5-chloro-1,6-dimethyl-4-hydroxy-2-oxo-1,2-dihydropyridine-3-carboxlate represented by the formula:

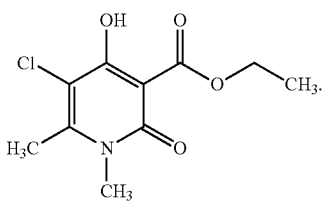

¹H-NMR(CDCl₃, TMS) δ(ppm): 1.45 (3H, t, J=7 Hz), 2.57 (3H, s), 3.54 (3H, s), 4.46 (2H, q, J=7 Hz), 14.10 (1H, s)

Reference Preparation Example 19

Using ethyl 2-fluoroacetoacetate in place of ethyl 2-chloroacetoacetate and according to the same manner as that of Reference Preparation Example 16, 5-fluoro-4-methyl-2H-1,3-oxazine-2,6(3H)-dione represented by the formula:

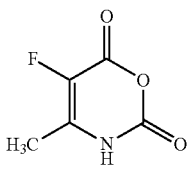

was obtained.

Reference Preparation Example 20

Using 5-fluoro-4-methyl-2H-1,3-oxazine-2,6(3H)-dione in place of 5-chloro-4-methyl-2H-1,3-oxazine-2,6(3H)-dione and according to the same manner as that of Reference Preparation Example 17, 5-fluoro-3,4-dimethyl-2H-1,3-oxazine-2,6(3H)-dione represented by the formula:

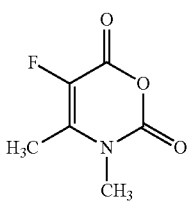

was obtained.

Reference Preparation Example 21

Using 5-fluoro-3,4-dimethyl-2H-1,3-oxazine-2,6(3H)-dione in place of 5-chloro-3,4-dimethyl-2H-1,3-oxazine-2,6(3H)-dione and according to the same manner as that of Reference Preparation Example 18, ethyl 5-fluoro-1,6-dimethyl-4-hydroxy-2-oxo-1,2-dihydropyridine-3-carboxylate represented by the formula:

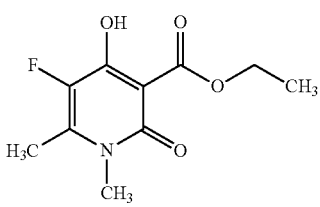

was obtained.

¹H-NMR(CDCl₃, TMS) δ(ppm): 1.45 (3H, d, J=7 Hz), 2.38 (3H, s), 3.46 (3H, s), 4.46 (2H, q, J=7 Hz), 13.67 (1H, s), 13.64 (1H, s)

Reference Preparation Example 22

14.4 g of a compound represented by the formula (XVII):

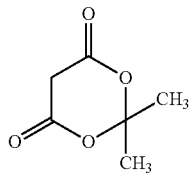

(XVII)

and 6.8 g of diketene were dissolved in 150 ml of acetonitrile, and 1.01 g of triethylamine was added at room temperature. The mixture was stirred at room temperature for 1 hour. Then, 15.5 g of a 40% methylamine solution in methanol was added to the mixture, then this was stirred at room temperature for 1 hour. Thereafter, the reaction mixture was cooled with an ice, and 30 ml of concentrated hydrochloric acid was added. The resulting crystal was collected by filtration and dried to obtain 17.6 g of 2,2-dimethyl-5-(1-hydroxy-3-methylamino-2-butenylidene)-1,3-dioxane-4,6-dione represented by the formula:

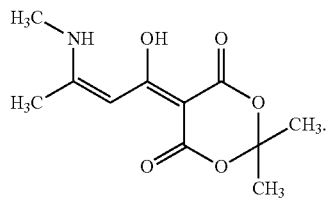

$^1$H-NMR(CDCl$_3$, TMS) δ(ppm): 1.70 (6H, s), 2.16 (3H, s), 3.09 (3H, d, J=4 Hz), 6.45 (1H, s), 8.82 (1H, br)

Reference Preparation Example 23

1.0 g of 2,2-dimethyl-5-(1-hydroxy-3-methylamino-2-butenylidene)-1,3-dioxane-4,6-dione was suspended in 20 ml of acetonitrile, 806 mg of N,N'-difluoro-2,2'-bipyridinium bis(tetrafluoroborate) was added thereto, and this was stirred at room temperature for 1 hour and at 50° C. for 30 minutes. The reaction mixture was added to 100 ml of ice water and extracted with 100 ml of chloroform twice. The organic layer was dried with anhydrous magnesium sulfate and concentrated, and the residue was subjected to silica gel column chromatography (eluent:ethyl acetate) to obtain 480 mg of 5-fluoro-1,6-dimethyl-4-hydroxy-2-oxo-1,2-dihydropyridine-3-carboxylic acid represented by the formula:

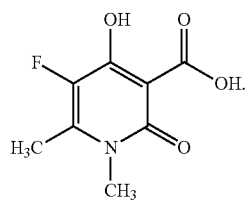

$^1$H-NMR(CDCl$_3$, TMS) δ(ppm): 2.47 (3H, s), 3.58 (3H, s), 13.89 (1H, br), 15.46 (1H, br)

Then, Formulation Examples will be shown. Part represents part by weight.

Formulation Example 1

Fifty parts of each of the present compounds 1 to 13, 3 parts of calcium ligninsulfonate, 2 parts of sodium laurylsulfate, and 45 parts of synthetic hydrous silicon oxide are ground and mixed well to obtain each wettable powder.

Formulation Example 2

Twenty parts of each of the present compounds 1 to 13, and 1.5 parts of sorbitan triolate are mixed with 28.5 parts of an aqueous solution containing 2 parts of polyvinyl alcohol, and finely-divided by a wet grinding method, 40 parts of an aqueous solution containing 0.05 part of xanthan gum and 0.1 part of aluminum magnesium silicate are added, 10 parts of propylene glycol is added and this is stirred and mixed to obtain each flowable preparation.

Formulation Example 3

Two parts of each of the present compounds 1 to 13, 88 parts of kaolin clay and 10 parts of talc are ground and mixed well to obtain each dust.

Formulation Example 4

Five parts of each of the present compounds 1 to 13, 14 parts of polyoxyethylene styryl phenyl ether, 6 parts of calcium dodecylbenzenesulfonate and 75 parts of xylene are mixed well to obtain each emulsifiable concentrate.

Formulation Example 5

Two parts of each of the present compounds 1 to 13, 1 part of synthetic hydrous silicon oxide, 2 parts of calcium ligninsulfonate, 30 parts of bentonite and 65 parts of kaolin clay are ground and mixed well, water is added, and the mixture is kneaded well, granulated and dried to obtain each granule.

Formulation Example 6

Ten parts of each of the present compounds 1 to 13, 35 parts of white carbon containing 50 parts of polyoxyethylene alkyl ether sulfate ammonium salt and 55 parts of water are mixed, and finely-divided by a wet grinding method to obtain each flowable preparation.

Then, Test Example demonstrates that the present compound is useful as an agricultural and horticultural fungicide. The present compound is indicated by a compound number.

Test Example 1

Cucumber Grey Mold Controlling Effect Test (Preventive Effect)

A plastic pot was charged with a sand loam, and cucumber (Name of plant variety: Sagamihanpaku) was seeded, and grown for 10 days in a greenhouse. Each flowable preparation of the present compounds 1 to 9, 12 to 17, 20, 23 to 25, 27 and 31 which had been obtained according to Preparation Example 6 was diluted with water to a predetermined concentration (500 ppm), to prepare a spraying solution. Each spraying solution was foliage-sprayed so that the solution was sufficiently adhered to cucumber leaves. After spraying, the cucumber was air-dried to an extent that the spraying solution on the leaves was dried, and a PDA medium containing a spore of cucumber grey mold (*Botrytis cinerea*) was placed on the cucumber leaves. After inoculation, the cucumber was placed at 12° C. under high humidity for 5 days, and controlling effect was investigated. As a result, an area of lesion in a plant treated with the present compounds 1 to 9, 12 to 17, 20, 23 to 25, 27 and 31 was 10% or less of an area of a lesion in a non-treated plant.

Test Example 2

Wheat Scab (*Fusarium culmorum*) Controlling Effect Test (Preventive Effect)

A plastic pot was charged with a sand loam, and a wheat (Name of plant variety: Shirogane komugi) was seeded, and was grown for 8 days in a greenhouse. Each flowable preparation of the present compound 12, 13 and 15 which had been obtained according to Preparation Example 6 was diluted with water to a predetermined concentration (500 ppm) to prepare a spraying solution. Each spraying solution was foliage-sprayed so that the solution was sufficiently adhered to the above adhered to wheat leaves. After spraying, the wheat was air-dried to an extent that the spraying solution on the leaves was dried, then a spore suspension of wheat scab (*Fusarium culmorum*) (containing about 2000000 spores per 1 ml of the suspension) was spraying-inoculated (at a ratio of about 2 ml per one plant). After inoculation, the wheat was placed at 23° C. under high humidity for 4 days, then placed in a 23° C. greenhouse for 3 days. Thereafter, the controlling effect was investigated. As a result, an area of a lesion in a plant treated with the present compound 12, 13 and 15 was 10% or less of an area of a lesion in a non-treated plant.

INDUSTRIAL APPLICABILITY

By using the present compound, a plant disease can be controlled.

The invention claimed is:

1. A carboxamide compound represented by the formula (I):

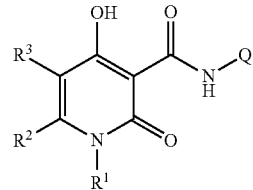

wherein Q represents a 2-thiazolyl group optionally substituted with at least one group selected from the group consisting of a halogen atom, a cyano group, a C1-C3 alkyl group and a C1-C3 haloalkyl group, $R^1$ represents a C1-C3 alkyl group or a C2-C5 alkoxyalkyl group, $R^2$ represents a hydrogen atom or a C1-C3 alkyl group, and $R^3$ represents a hydrogen atom, a halogen atom or a C1-C3 alkyl group.

2. The carboxamide compound according to claim 1, wherein $R^3$ is a hydrogen atom or a C1-C3 alkyl group.

3. The carboxamide compound according to claim 1, wherein $R^3$ is a hydrogen atom or a halogen atom.

4. A plant disease controlling composition comprising the carboxamide compound as defined in claim 1 as an active ingredient, and an inert carrier.

* * * * *